United States Patent [19]

Dean

[11] Patent Number: 4,761,173
[45] Date of Patent: Aug. 2, 1988

[54] HERBICIDAL HETEROCYCLIC SULFONAMIDES

[75] Inventor: Thomas R. Dean, Wilmington, Del.

[73] Assignee: E. I. Du Pont de Nemours and Company, Wilmington, Del.

[21] Appl. No.: 29,731

[22] Filed: Mar. 24, 1987

Related U.S. Application Data

[63] Continuation-in-part of Ser. No. 859,999, May 2, 1986, abandoned.

[51] Int. Cl.$^4$ .................. C07D 239/38; C07D 239/56; C07D 401/12; A01N 43/54
[52] U.S. Cl. .................................... 71/92; 71/90; 544/300; 544/301; 544/310; 544/311; 544/316; 544/317
[58] Field of Search ...................... 71/90, 92; 544/300, 544/301, 310, 311, 312, 316, 317, 326, 328, 327, 329

[56] References Cited

FOREIGN PATENT DOCUMENTS 833849 1/1984 South Africa .
848844 5/1985 South Africa .

OTHER PUBLICATIONS

Roblin Jr. and Clapp, James W., "The Preparation of Heterocyclic Sulfonamides", J. Am. Chem. Soc., 72, 4890, (1950).
Miller, William H., et al., "Heterocyclic Sulfonamides as Carbonic Anhydrase Inhibitors", J. Amer. Chem. Soc., 72, 4893, (1950).

Primary Examiner—John M. Ford

[57] ABSTRACT

Substituted heterocyclic sulfonamides having herbicidal activity and agriculturally useful compositions comprising such compounds.

41 Claims, No Drawings

HERBICIDAL HETEROCYCLIC SULFONAMIDES

This application is a continuation-in-part of application Ser. No. 859,999, filed May 2, 1986, now abandoned.

BACKGROUND OF THE INVENTION

U.S. Ser. No. 551,758 filed on Nov. 14, 1983 discloses substituted 1,2,4-triazolo[1,5-a]pyrimidine-2-sulfonamides of the formula

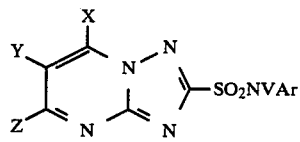

as herbicides and plant growth regulators. Ar is an aromatic or heteroaromatic ring system.

Articles by R. O. Roblin et al. in *J. Am. Chem. Soc.* 72, 4890, (1950) and W. H. Miller et al. in *J. Am. Chem. Soc.* 72, 4893, (1950) describe the preparation of 4,6-dimethylpyrimidine-2-sulfonamide and its activity as an inhibitor of the mammalian enzyme carbonic anhydrase. Herbicidal utility is not discussed.

South African Application 83/3849 published on May 27, 1983 discloses substituted pyrimidine-2-sulfonamides as intermediates for the preparation of herbicidal sulfonylureas.

SUMMARY OF THE INVENTION

This application pertains to heterocyclic sulfonamides having the formula

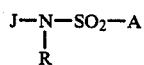   I and to agriculturally suitable compositions containing them and their method-of-use as preemergent and/or postemergent herbicides or plant growth regulants.

In the above formula

R is H, $C(O)R_1$, $CO_2R_1'$, $C(O)NR_1R_2$, $C(S)NR_1R_2$, $C_3$-$C_4$ alkenyl or $C_3$-$C_4$ alkynyl;

$R_1$ is $C_1$-$C_4$ alkyl; $C_1$-$C_4$ haloalkyl; $C_2$-$C_4$ alkoxyalkyl; $C_3$-$C_4$ alkenyl; $C_3$-$C_4$ alkynyl or phenyl optionally substituted by F, Cl, Br, $CH_3$ or $OCH_3$;

$R_2$ is H or $C_1$-$C_2$ alkyl;

J is

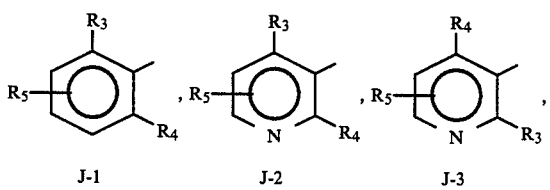

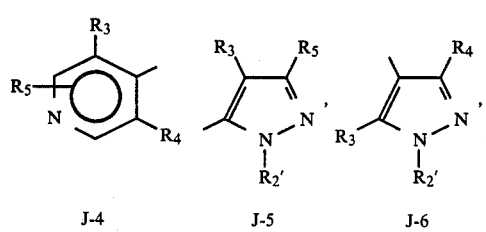

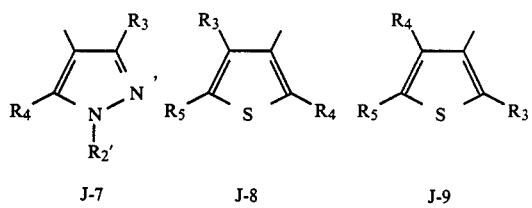

$R_3$ is F; Cl; Br; I; $NO_2$; $ER_1''$; $C_1$-$C_4$ alkyl; $SO_2NR_1'''R_2$; $C_1$-$C_4$ alkyl substituted by at least one F, Cl, Br or $C_1$-$C_3$ alkoxy; $C(O)R_1''''$; $CO_2R_1'$; $OSO_2R_1''$;

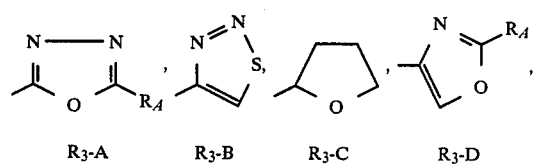

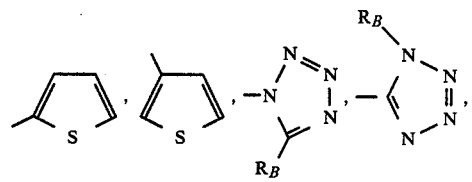

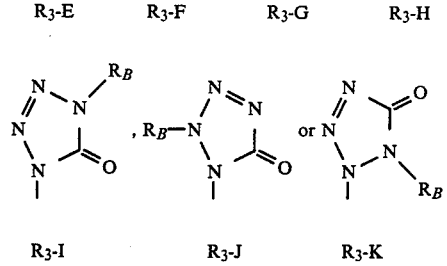

E is O, S, SO or $SO_2$;

$R_4$ is F; Cl; Br; I; $NO_2$; $ER_1''$; $C_1$-$C_4$ alkyl; $C_1$-$C_4$ alkyl substituted by at least one F, Cl, Br or $C_1$-$C_3$ akoxy or $OSO_2R_1''$;

$R_5$ is H; F; Cl; Br; $NO_2$; $N(CH_3)_2$; $E(C_1$-$C_2$ alkyl); $C_1$-$C_2$ alkyl or $C_1$-$C_2$ alkyl substituted by at least one F, Cl, Br or $OCH_3$.

$R_1'$ is $C_1$-$C_4$ alkyl, $C_2$-$C_4$ haloalkyl, $C_2$-$C_4$ alkoxyalkyl, $C_3$-$C_4$ alkenyl or $C_3$-$C_4$ alkynyl;

$R_1''$ is $C_1$-$C_4$ alkyl, $C_1$-$C_4$ haloalkyl, $C_2$-$C_4$ alkoxyalkyl, $C_3$-$C_4$ alkenyl or $C_3$-$C_4$ alkynyl;

$R_1'''$ is $C_1$-$C_3$ alkyl, allyl or propargyl;

$R_1''''$ is $C_1$-$C_4$ alkyl, $C_1$-$C_4$ haloalkyl, $C_2$-$C_4$ alkoxyalkyl, $C_3$-$C_4$ alkenyl, $C_3$-$C_4$ alkynyl, cyclopropyl or cyclopropylmethyl;

$R_2'$ is H, $C_1$-$C_3$ alkyl, allyl, propargyl, $CF_3CH_2$, or phenyl;

$R_A$ is H or $CH_3$;

$R_B$ is H, $CH_3$ or $CH_2CH_3$.

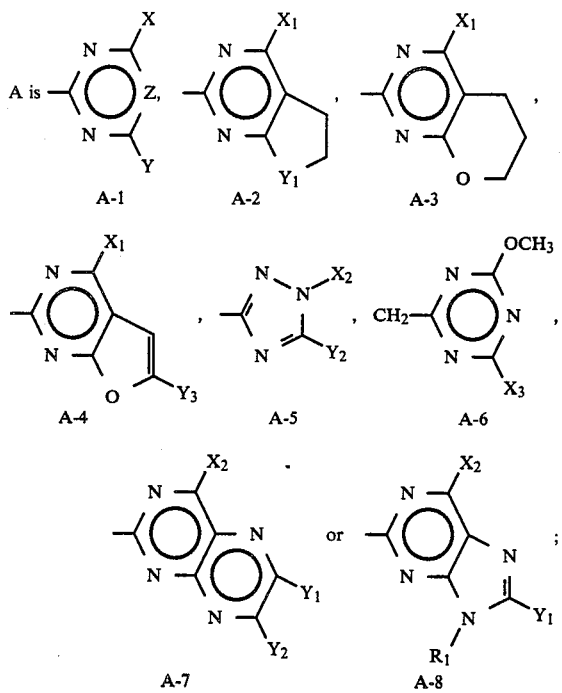

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino or $C_3$-$C_5$ cycloalkyl;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, azido, $C_2$-$C_4$ alkynyl, cyano,

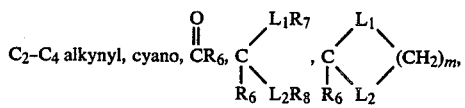

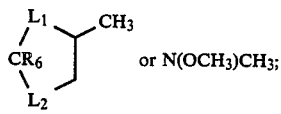

or N(OCH$_3$)CH$_3$;

m is 2 or 3;
$L_1$ and $L_2$ are independently O or S;
$R_6$ is H or $C_1$-$C_3$ alkyl;
$R_7$ and $R_8$ are independently $C_1$-$C_3$ alkyl;
Z is CH, N, CCH$_3$, CC$_2$H$_5$, CCl or CBr;
$Y_1$ is O or CH$_2$;
$X_1$ is CH$_3$, OCH$_3$, OC$_2$H$_5$ or OCF$_2$H;
$X_2$ is CH$_3$, C$_2$H$_5$ or CH$_2$CF$_3$;
$Y_2$ is OCH$_3$, OC$_2$H$_5$, SCH$_3$, SC$_2$H$_5$, CH$_3$ or CH$_2$CH$_3$;
$X_3$ is CH$_3$ or OCH$_3$;
$Y_3$ is H or CH$_3$;
provided that
(a) when X is Cl, F, Br or I, then Z is CH and Y is OCH$_3$, OC$_2$H$_5$, N(OCH$_3$)CH$_3$, NHCH$_3$, N(CH$_3$)$_2$ or OCF$_2$H;

(b) when X or Y is C$_1$ haloalkoxy, then Z is CH; and (c) when the total number of carbon atoms of X and Y is greater than four, then the combined number of carbons of $R_3$, $R_4$ and $R_5$ is less than or equal to six.

Preferred for reasons of their higher herbicidal activity, greater plant growth regulant activity or more favorable ease of synthesis are:

(1) Compounds of Formula I wherein
R is H;
X is CH$_3$, OCH$_3$, OCH$_2$CH$_3$, Cl, F, Br, I, OCF$_2$H, CH$_2$F, CF$_3$, OCH$_2$CH$_2$F, OCH$_2$CHF$_2$, OCH$_2$CF$_3$, CH$_2$Cl or CH$_2$Br;
Y is H, CH$_3$, OCH$_3$, OCH$_2$CH$_3$, CH$_2$OCH$_3$, NHCH$_3$, N(OCH$_3$)CH$_3$, N(CH$_3$)$_2$, CH$_2$CH$_3$, CF$_3$, SCH$_3$, OCH$_2$CH=CH$_2$, OCH$_2$C≡CH, CH$_2$OCH$_2$CH$_3$, OCH$_2$CH$_2$OCH$_3$, CH$_2$SCH$_3$, CH$_2$SCH$_2$CH$_3$, OCH$_2$CH$_2$OCH$_3$,

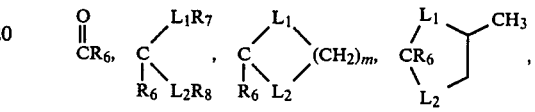

OCF$_2$H, SCF$_2$H, C≡CH or C≡CCH$_3$; and
A is A-1, A-2, A-3, A-4, A-5 or A-6 and J is J-1, J-2, J-3, J-4, J-5, J-6, J-7, J-8 and J-9.

Especially preferred are compounds wherein J is J-1 and
A is A-1;
$R_5$ is H, F, Cl, Br, CH$_3$, OCH$_3$ or SCH$_3$; and
Z is CH or N and, more particularly, where
X is CH$_3$, OCH$_3$, OCH$_2$CH$_3$, Cl or $C_1$-$C_2$ haloalkoxy and
Y is CH$_3$, OCH$_3$, CH$_2$CH$_3$, CH$_2$OCH$_3$, $C_1$-$C_2$ haloalkoxy, NHCH$_3$ or N(CH$_3$)$_2$ and further where
$R_5$ is H;
$R_3$ is F, Cl, Br, E($C_1$-$C_2$ alkyl), $C_1$-$C_2$ alkyl, SO$_2$NHCH$_3$, SO$_2$N(CH$_3$)$_2$, $C_1$-$C_2$ alkyl substituted by at least one F, Cl, Br or OCH$_3$, C(O)($C_1$-$C_2$ alkyl), CO$_2$($C_1$-$C_2$ alkyl) or OSO$_2$($C_1$-$C_2$ alkyl); and
$R_4$ is F, Cl, Br, E($C_1$-$C_2$ alkyl), $C_1$-$C_2$ alkyl, SO$_2$NHCH$_3$, SO$_2$N(CH$_3$)$_2$, $C_1$-$C_2$ alkyl substituted by at least one F, Cl, Br or OCH$_3$, C(O)($C_1$-$C_2$ alkyl), CO$_2$($C_1$-$C_2$ alkyl) or OSO$_2$($C_1$-$C_2$ alkyl).

Specific examples of the foregoing preferred for reasons of greatest ease of synthesis and/or greatest herbicidal efficacy are N-(2-chloro-6-methylphenyl)-4,6-dimethyl-2-pyrimidinesulfonamide; N-(2,6-dichlorophenyl)-4,6-dimethyl-2-pyrimidinesulfonamide; N-(2,6-dichloro-3-methylphenyl)-4,6-dimethyl-2-pyrimidinesulfonamide; N-(2,6-dichlorophenyl)-4,6-dimethoxy-2-pyrimidinesulfonamide; and N-(2,6-dichlorophenyl)-4-methoxy-6-methyl-2-pyrimidinesulfonamide.

DETAILED DESCRIPTION OF THE INVENTION

As used herein "alkyl", either alone or in compound words such as "alkylthio" or "haloalkyl", denotes straight chain or branched alkyl, e.g. methyl, ethyl, n-propyl, isopropyl or the different butyl isomers.

Alkoxy means methoxy, ethoxy, n-propyloxy, isopropyloxy and the different butyloxy isomers.

Alkenyl means straight chain or branched alkenes, e.g. vinyl, 1-propenyl, 2-propenyl, 3-propenyl, isopropenyl and the different butynyl isomers.

Alkynyl means straight chain or branched alkynes, e.g. ethynyl, 1-propynyl, 2-propynyl and the different butynyl isomers.

Alkylsulfonyl means methylsulfonyl, ethylsulfonyl or the different propyl isomers.

Cycloalkyl means cyclopropyl, cyclobutyl, cyclopentyl.

"Halogen", either alone or in compound words such as "haloalkyl", means fluorine, chlorine, bromine or iodine. When used in compound words such as "haloalkyl" means partially or fully substituted with the same or different halogen atoms. Examples of haloalkyl include $CH_2CH_2F$, $CF_2CF_3$ and $CH_2CHFCl$.

The total number of carbon atoms in a substituent group is indicated by subscript on the C. For example, $C_1$-$C_3$ alkoxy would designate methoxy through propoxy.

Synthesis

The compounds of Formula I can be prepared by one or more of the following methods described in Equations 1 to 4.

As shown in Equation 1, compounds of Formula I can be prepared by reacting substituted aryl amines of Formula (1) with a sulfonyl halide of Formula (2) under basic conditions.

Equation 1

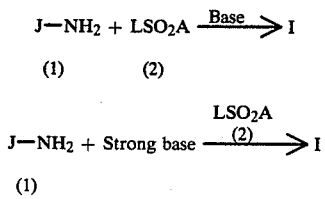

wherein

J, A and I are as previously defined; and
L is Cl or F.

In Equation 1a, sulfonyl halides of Formula (2) are mixed together with aryl amines of Formula (1) in solvents such as dichloromethane, 1,2-dichloroethane, tetrahydrofuran, acetonitrile, or pyridine. The coupling reaction is catalyzed by the addition of an appropriate base such as pyridine, 4-dimethylaminopyridine, triethylamine, or diisopropylethylamine, at temperatures ranging between $-20°$ C. and reflux. In most cases the reaction is carried out with an excess of aryl amine in pyridine as solvent with 4-dimethylamino-pyridine or diisopropylethylamine added as the catalyst.

When the reaction is judged to be complete the reaction mixture is concentrated and the residue is dissolved in dilute aqueous NaOH. The excess aryl amine is extracted into diethylether and the aqueous layer is acidified with dilute aqueous HCl. The desired product is collected by filtration.

Relatively unreactive aryl amines of Formula (1) can be coupled with sulfonyl halides of Formula (2) using conditions shown in Equation 1b. The aryl amine is deprotonated with a strong base such as n-butyl lithium, lithium diisopropylamide (LDA), lithium bis(trimethylsilyl)amide, potassium or sodium hydride in an inert ethereal solvent such as tetrahydrofuran (THF), diethyl ether, or dimethoxyethane (DME) and the mixture is added to the sulfonyl halide in the same solvent at temperatures ranging between $-78°$ C. and $0°$ C. The desired product is isolated in the same manner described in Equation 1a.

Some sulfonyl halides of Formula (1) are unstable under the reaction conditions described in Equations 1a and 1b and an alternative method is used as described in Equations 2a and 2b.

Equation 2

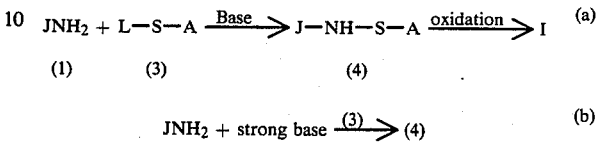

wherein

J, A and I are as previously defined; and
L is Cl or Br.

Aryl amines of Formula (1) are reacted with sulfenyl halides of Formula (3) to form sulfenamides of Formula (4) under the same conditions described in Equations 1a and 1b. The resultant sulfenamides of Formula (4) may be oxidized using a variety of oxidants such as 5% aqueous potassium permanganate solution as described in *Bull. Chem. Soc.*, Japan 46, 1890–1891 (1973) or metachloroperoxybenzoic acid as described in *Synthesis* (1977), 798–800 or activated magnesium dioxide as described in *J. Fluorine Chemistry*, 5, 83–86 (1975). Another useful reference is found in *J. Amer. Chem. Soc.*, 76, 6052 (1954).

Sulfonamides of Formula I with the heterocyclic ring substituted with alkoxy, mercapto or amino groups can be prepared from sulfonamides of Formula Ia with the heterocyclic ring substituted with readily displaceable groups, such as halogen. This process is described in Equation 3.

Equation 3

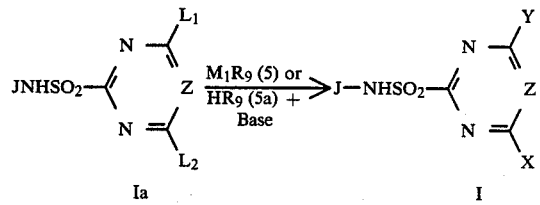

wherein

J, I, X, Y and Z are as previously defined;
$L_1$ is F, Cl or Br;
$L_2$ is X or Y;
$M_1$ is Li, Na or K; and
$R_9$ is alkoxy, alkylthio, amino, alkylamino or azido.

For example, sulfonamides of Formula Ia are dissolved in a polar aprotic solvent such as N,N-dimethylformamide (DMF), dimethylsulfoxide (DMSO), dimethoxyethane (DME), N-methyl-2-pyrrolidinone (NMP), and in some cases alcoholic solvents are desired such as methanol or ethanol. Then at least two equivalents of a nucleophile is added as its metal salt of Formula (5) or in its neutral form of Formula (5a) in the presence of an appropriate base such as potassium carbonate, potassium hydroxide, pyridine, diisopropylethylamine, or potassium tertiary butoxide. The reaction is conducted at temperatures ranging from $0°$ C. to $80°$ C.

When the reaction is judged to be complete, the reaction mixture is poured onto ice and acidified. The desired product is collected by filtration.

N-substituted sulfonamides of Formula I can be prepared from the corresponding unsubstituted sulfonamides of Formula I as described in Equation 4.

Equation 4

$$\underset{I}{\underset{H}{J-N}-SO_2A} + Base \xrightarrow{E_1 (6)} \underset{I, R \neq H}{\underset{R}{J-N}-SO_2A}$$

wherein

J, A, I, R, $R_1$ and $R_2$ are as previously defined;

$E_1$ is $LC(O)R_1$, $LCO_2R_1'$, $LC(O)NR_1R_2$, $LC(S)NR_1R_2$, $OCNR_1$, $SCNR_1$, $C_3$–$C_4$ haloalkenyl, $C_3$–$C_4$ haloalkynyl or $CH_2O$; and L is Cl or Br.

Unsubstituted sulfonamides of Formula I are deprotonated with an appropriate base such as sodium methoxide, potassium tert-butoxide, potassium or sodium carbonate, potassium or sodium hydride, or pyridine in an appropriate solvent such as tetrahydrofuran (THF), dimethoxyethane (DME), acetonitrile, methanol, tertiary butanol, N,N-dimethylformamide (DMF), or dimethylsulfoxide (DMSO). Then the appropriate electrophile of Formula (6) is added and the reaction is allowed to proceed at temperatures ranging from 0° C. to reflux.

When the reaction is judged to be complete the mixture is poured onto ice-water and the desired product is either collected as a solid or extracted into an appropriate solvent such as diethylether or ethyl acetate and isolated after the evaporation of solvent.

Many of the anilines of Formula (1) are known in the literature and those that are not can be prepared by one skilled in the art.

Heterocyclic sulfonyl halides of Formula (2) may be prepared by one or more of the methods outlined in Equations 5 to 7.

Sulfonyl halides of Formula (2) can be prepared by the oxidative chlorination of mercapto derivatives of Formula (7) or (7a) as described in Equation 5. A variety of conditions can be used depending on the nature of the heterocyclic ring system. For many of these sulfonyl halides, simple chlorination in the presence of aqueous HCl furnishes the desired sulfonyl chloride as shown in Equation 5a.

The oxidation can also be accomplished using sodium hypochlorite as the oxidant in a two phase system of aqueous HCl and methylene chloride as shown in Equation 5b. Or for some cases the oxidation is done with chlorine in the presence of fluoride ion and sulfonyl fluorides of Formula (2) are the products as shown in Equation 5c. Sulfonyl halides of Formula (2) with substituents that are strong electron donators can be prepared by the oxidation of sulfoxides of Formula (7a) using the same condition described in Equations 5a, b and c as shown in Equation 5d. Sulfoxides of Formula (7a) can be prepared from the corresponding sulfides of Formula (7) using a variety of conditions that are well known in the literature.

Equation 5

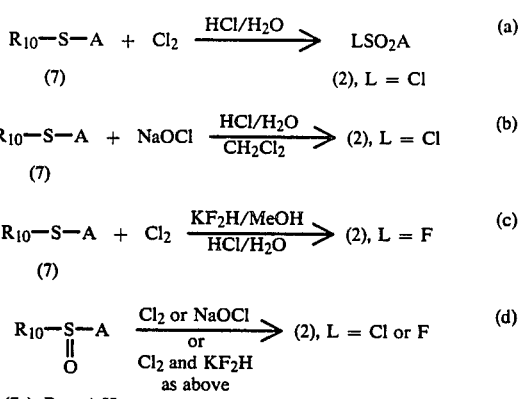

wherein

A is as previously defined;

$R_{10}$ is H, $C_2$–$C_4$ alkyl, benzyl or p-methoxybenzyl; and

L is Cl or F.

Heterocyclic mercapto derivatives of Formula (7) or (7b) are dissolved or suspended in aqueous HCl ranging from 1N to 6N and chlorine gas is bubbled through the mixture at temperatures ranging from 0° C. to 25° C. for time periods ranging from 10 minutes to 3 hours. When the reaction is judged complete (normally by the persistence of the yellow-green color of excess chlorine) the mixture is poured onto ice-water and the desired product precipitates from solution. The solid is collected, washed with water and air dried.

For those examples where the sulfonyl chloride is an oil, the aqueous solution is extracted with an appropriate solvent such as dichloromethane, washed with water and brine, dried (magnesium or sodium sulfate) and then concentrated. In either case, the resultant sulfonyl chlorides of Formula (2) are usually pure enough for immediate use.

In some cases, sulfonyl chlorides of Formula (2) start to decompose at temperatures above 0° C. In those cases, the reaction workup that is described above is altered. Instead of pouring the reaction mixture onto ice-water, it is poured directly into a suitable solvent such as dichloromethane or chloroform which has been cooled to 0° C. The mixture is separated and washed repeatedly with cold water followed by brine. The mixture is then dried using magnesium or sodium sulfate and concentrated while keeping the solution cold. The crude sulfonyl chloride is used directly as described in Equation 1.

Heterocyclic mercapto derivatives of Formula (7) or (7a) are added to a biphasic mixture of aqueous HCl ranging from 1N to 6N and methylene chloride at temperatures ranging from −5° C. to 0° C. An aqueous solution of sodium hypochlorite is added dropwise keeping the temperature at or below 0° C. When the reaction is judged to be complete the layers are separated and the organic layer is washed with saturated sodium bicarbonate and then brine. The organics are dried using magnesium sulfate while keeping the solution cold and the crude sulfonylΔ chloride solution is used directly.

It is often more expedient to prepare sulfonyl fluorides of Formula (2). In these cases the sulfonyl fluoride is prepared by oxidative chlorination in much the same way as described for Equation 5a with the exception that fluoride ion is present in solution as shown in Equation 5c. This procedure is described in *J. C. S. Perkin I*, 522 (1972).

In most cases, the sulfonyl chlorides of Formula (2) can be converted into the corresponding sulfonyl fluoride using methods known in the literature. This reaction is shown in Equation 6.

Equation 6

$$ClSO_2A \xrightarrow{F^{\ominus}} FSO_2A$$
$$(2) \quad\quad\quad (2)$$

wherein A is as previously defined.

Sulfonyl halides of Formula (2) can be prepared from the salts of sulfonic acids of Formula (8) or sulfinic acids of Formula (9) as shown in Equations 7a and 7b.

Equation 7

$$MO_3S-A \xrightarrow[\text{or POCl}_3]{PCl_5} (2), L = Cl \quad (a)$$
$$(8)$$

$$MO_2S-A \xrightarrow{NCS} (2), L = Cl \quad (b)$$
$$(9)$$

wherein
A is as previously defined;
M is Li, Na or K; and
L is Cl.

Metal salts of sulfonic acids of Formula (8) are treated with phosphorus pentachloride or phosphorus oxychloride at temperatures ranging from 25° C. to refluxing. When the reaction is judged to be complete the mixture is poured onto ice and the desired sulfonyl chlorides of Formula (2) are collected as solids or extracted into an appropriate solvent in much the same way as described for Equation 5.

The metal salts of sulfonic acids of Formula (8) can be prepared by methods known in the literature, see *Bull. Chem. Soc. Japan*, 46, 1890–1891 (1973).

Metal salts of sulfinic acids of Formula (9) can be converted to sulfonyl chlorides at much lower temperatures than the corresponding sulfonic acids. For sulfonyl chlorides of Formula (2) that are relatively unstable at temperatures above 0° C. this procedure is advantageous. This procedure is described in U.S. Pat. No. 4,547,217.

Metal salts of sulfinic acids of Formula (9) may be prepared from bromoheterocycles of Formula (11) by a method similar to that described in U.S. Pat. No. 4,547,217 as shown in Equation 8.

Equation 8

$$Br-A + BuLi \xrightarrow[-100° C.]{SO_2} LiO_2S-A$$
$$(11) \quad\quad\quad\quad\quad\quad\quad (9)$$

wherein A is as previously defined.

The heterocyclic mercapto derivatives of Formula (7) can be prepared in a number of ways as described in Equations 9 and 10. This wide variety of available synthetic methods allows for the efficient preparation of all the chemically sensitive groups embodied in sulfonyl halides of Formula (2).

A number of heterocyclic mercapto compounds of Formula (7) are commercially available as the simple unsubstituted mercapto compound of Formula (7) where $R_{10}$ is hydrogen. When necessary, these materials can be derivatized by the alkylation of the mercapto moiety using procedures well known in the literature, *J. Med. Chem.*, 27, 1621–1629 (1984).

Many of the mercapto derivatives of Formula (7) where $R_{10}$ is hydrogen can be prepared from the corresponding hydroxy heterocycles of Formula (10) as described in Equations 9a, 9b and 9c.

Equation 9

$$HO-A \xrightarrow[\Delta]{PS_5} HS-A \quad (a)$$
$$(10) \quad\quad\quad (7)$$

$$(10) \xrightarrow[C_6H_5N(C_2H_5)_2]{POX_3} X-A \quad (b)$$
$$\quad\quad\quad\quad\quad\quad (11)$$

$$X-A \xrightarrow[\text{Base}]{HSR_{10} (12)} R_{10}-S-A \quad (c)$$
$$(11) \quad\quad\quad\quad\quad (7)$$

wherein
A is as previously defined;
X is Cl or Br; and
$R_{10}$ is H, $C_2$–$C_3$ alkyl, benzyl or p-methoxybenzyl.

Heterocyclic mercapto compounds of Formula (7) can be prepared from the hydroxy heterocycles of Formula (10) by the action of phosphorus pentasulfide in β-picoline at reflux as described in *Bull. Chem. Soc. Japan*, 46, 1890–1891 (1973), Equation 9a. Alternatively, hydroxy heterocycles of Formula (10) can be converted into the corresponding haloheterocycle of Formula (11) by the action of phosphorousoxychloride or bromide in the presence of N,N-diethylaniline as described in *J. Med. Chem.* 27, 1621–1629 (1984), Equation 9b.

The haloheterocycle of Formula (11) is treated with a suitable mercaptan of Formula (12) in the presence of a base such as potassium tert-butoxide, potassium or sodium carbonate, potassium or sodium hydride or sodium methoxide in an appropriate solvent such as N,N-dimethylformamide (DMF), tetrahydrofuran (THF), or dimethoxyethane (DME) at temperatures ranging from −78° C. to 25° C., Equation 9c.

When the displacement reaction is judged to be complete, the reaction mixture is poured onto ice-water and the desired product is isolated by extraction with an appropriate solvent such as diethylether, dichloromethane or ethyl acetate. The solvent is dried (magnesium or sodium sulfate) and the product is isolated after the evaporation of solvent.

Heterocyclic mercapto compounds of Formula (7) where $R_{10}$ is hydrogen can be prepared from corresponding compounds of Formula (7) where $R_{10}$ is the 4-methoxybenzyl group by the action of trifluoroacetic acid in the presence of anisole as described in *J. Med. Chem.*, 27, 1621–1629 (1984), Equation 10.

Equation 10

$$CH_3O-\langle\bigcirc\rangle-CH_2-S-A \xrightarrow{TFA,\ \langle\bigcirc\rangle\text{-}O\text{-}} H-S-A$$

(7)　　　　　　　　　　　　(7)

wherein A is as previously defined.

Most of the haloheterocycles of Formula (11) can be prepared from the corresponding amino heterocycle of Formula (12) using procedures well known in the literature and is described in *J. Chem. Soc. C*, 2031 (1966), Equation 11.

Equation 11

$$H_2N-A\ +\ NaNO_2\ \xrightarrow{HX}\ X-A$$

(12)　　　　　　　　　(11)

wherein
A is as previously defined; and
X is Cl or Br.

The amino heterocycles of Formula (12) are well known in the literature and have been used extensively in the preparation of sulfonylureas. The synthesis of amino heterocycles of Formula (12) can be found in "The Chemistry of Heterocyclic Compounds," a series published by Interscience Publishers, Inc., New York and London. U.S. Pat. No. 4,547,217 describes the synthesis of many of the bicyclic amino heterocycles of Formula (12).

Using the procedures described in Equations 1-11, the compounds in Tables 1-15 can be prepared.

EXAMPLE 1

N-(2-Chloro-6-methylphenyl)-4,6-dimethyl-2-pyrimidinesulfonamide

To a solution of 2-chloro-6-methylaniline (0.5 g, 3.5 mmol) in dimethoxyethane (15 mL) cooled to 0° C. was added butyl lithium (2.2 mL, 3.5 mmol) and the mixture was allowed to stir for 15 minutes. Then 4,6-dimethyl-2-pyrimidinesulfonyl fluoride (0.66 g, 3.5 mmol), prepared according to Brown and Hoskins, *J. Chem. Soc. Perkin* 1, 522-527 (1972) was added. The mixture stirred with warming to 25° C. for 1 hour. The mixture was concentrated and the residue triturated with butyl chloride. The resultant solid was acidified with 1N HCl and the solid was filtered. The product was a yellow-brown solid, m.p. 215°-219° C. NMR (200 MHZ) D$_6$-Acetone: δ 8.2 (bs, 1H), 7.4 (s, 1H), 7.2 (bs, 3H), 2.5 (s, 6H) and 2.35 (s, 3H).

EXAMPLE 2

N-(2,6-Dichlorophenyl)-4,6-dimethyl-2-pyrimidinesulfonamide

To a solution of 2,6-dichloroaniline (1.0 g, 6.2 mmol) in dimethoxyethane (25 mL) was added butyl lithium (3.9 mL, 6.24 mmol). After 15 minutes, the solution was cooled to −30° and 4,6-dimethyl-2-pyrimidinesulfonyl fluoride (1.18 g, 6.2 mmol) was added. The mixture stirred for 12 hours with warming to 25° C. The mixture was concentrated and the residue was treated with 1N NaOH (2 mL) and extracted with ethyl acetate. The aqueous layer was acidified with 1N HCl and a solid was collected, m.p. 261°-263° C. NMR (90 MHZ) D$_6$-Acetone: δ 7.5 (m, 4H) and 2.5 (s, 6H).

EXAMPLE 3

N-(2,6-Dichloro-3-methylphenyl)-4,6-dimethyl-2-pyrimidinesulfonamide

This material was prepared from 2,6-dichloro-3-methylaniline and 4,6-dimethyl-2-pyrimidinesulfonyl fluoride following the general procedure described in Example 2. The desired product was isolated as a solid, m.p. 234°-235°. NMR (90 MHZ) D$_6$-Acetone: δ 7.4 (d, 2H), 7.3 (s, 1H), 2.5 (s, 6H) and 2.3 (s, 3H).

EXAMPLE 4

N-(2,6-dichlorophenyl)-4-6-dimethoxy-2-pyrimidinesulfonamide

A solution of 4,6-dimethoxy-2[(4-methoxybenzyl)thio]pyrimidine (10.0 g, 34.2 mmol) (prepared according to a modified procedure described by d'Atri in *J.Med. Chem.* 1984, 27, 1621-1629) in tetrahydrofuran (THF) (100 mL) and isopropyl alcohol (5 mL) containing solid sodium bicarbonate (5 g) was cooled to −78° C. by means of a dry ice/acetone bath. A solution of 3-chloroperoxybenzoic acid (MCPBA) (7.1 g, 35 mmol) dissolved in tetrahydrofuran (THF) (25 mL) was added dropwise. After the addition was completed the mixture was allowed to warm to 25° C. The remaining peroxide was decomposed by treatment with aqueous sodium bisulfite. The organic layer was diluted with diethyl ether and washed with 5% sodium bicarbonate and dried with magnesium sulfate. The desired product was obtained as an oil and was used directly in the next step. Ten grams of this material was oxidatively chlorinated using the same procedure described in Example 1 and 2.0 g of the requisite sulfonyl fluoride was obtained and used directly in the next reaction.

The desired pyrimidinesulfonamide was prepared from 2,6-dichloroaniline and the above sulfonyl fluoride as described in Example 1. The desired product was isolated as a solid, m.p. 185° C., NMR (200 MHZ) D$_6$-acetone: δ 7.4 (d, 1H), 7.3 (d, 1H), 7.2 (dd, 1H), 6.7 (bs, 1H), 3.95 (s, 6H).

| Compounds in Tables 1-15 | |
|---|---|
| Formula 1 | ![structure with R3, R5, R4 on phenyl, N-SO2 linked to pyrimidine with OCH3, OCH3] |
| Formula 2 | ![structure with R3, R5, R4 on phenyl, N-SO2 linked to pyrimidine with OCH3, CH3] |

-continued
Compounds in Tables 1–15
Formula 3
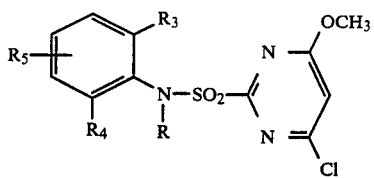
Formula 4
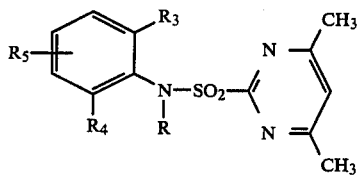
Formula 5
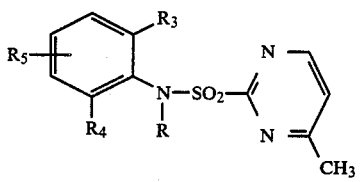
Formula 6
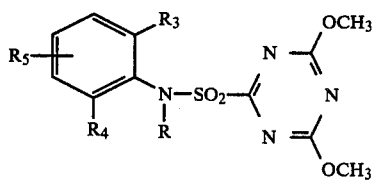
Formula 7
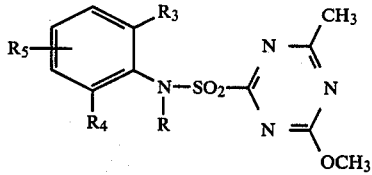
Formula 8
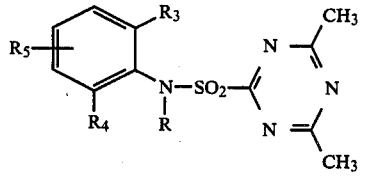
Formula 9
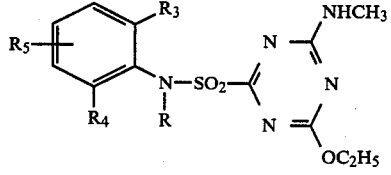
Formula 10
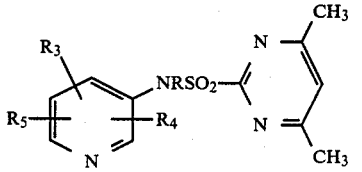
-continued
Compounds in Tables 1–15
Formula 11
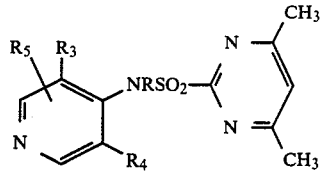
Formula 12
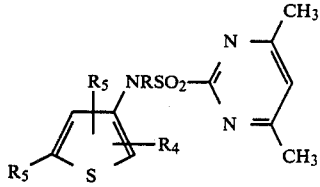
Formula 13
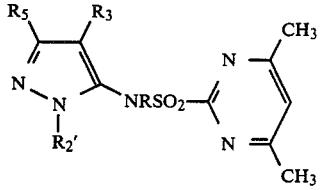
Formula 14
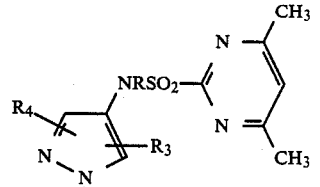
Formula 15
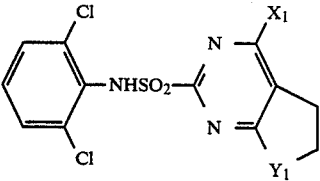
Formula 16
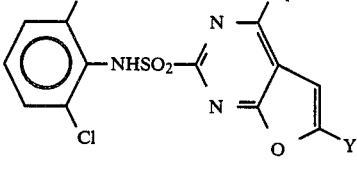
Formula 17
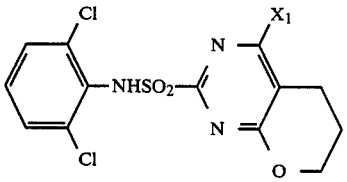
Formula 18
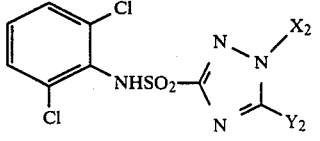

-continued

Compounds in Tables 1-15

Formula 19

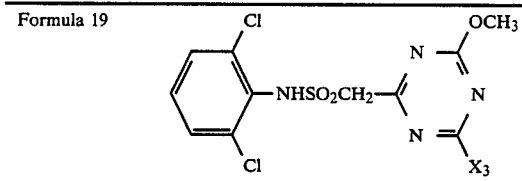

Formula 20

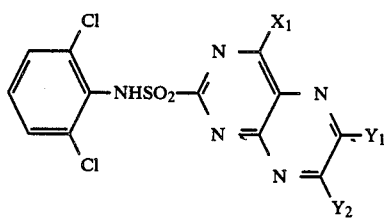

Formula 21

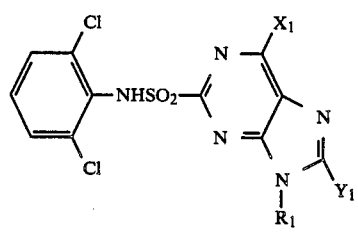

TABLE 1

Formula 1

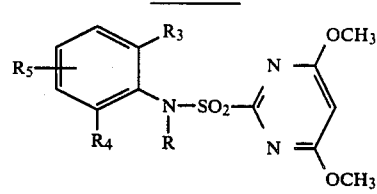

| R | R$_3$ | R$_4$ | R$_5$ | m.p. (°C.) |
|---|---|---|---|---|
| H | 2-Cl | 6-Cl | H | 185° |
| H | 2-Cl | 6-Cl | 3-CH$_3$ | |
| H | 2-Cl | 6-Cl | 3-Cl | |
| H | 2-Cl | 6-COOCH$_3$ | H | |
| H | 2-Cl | 6-Br | H | |
| H | 2-Cl | 6-CH$_3$ | H | |
| H | 2-Cl | 6-CH$_2$OCH$_3$ | H | |
| H | 2-Cl | 6-CH$_2$F | H | |
| H | 2-Cl | 6-F | H | |
| H | 2-Cl | 6-SO$_2$CH$_3$ | H | |
| H | 2-Cl | 6-OSO$_2$CH$_3$ | H | |
| H | 2-Cl | 6-SO$_2$N(CH$_3$)$_2$ | H | |
| H | 2-Cl | 6-SOC$_2$H$_5$ | H | |
| H | 2-Cl | 6-OCH$_3$ | H | |
| H | 2-Cl | 6-CO$_2$C$_2$H$_5$ | H | |
| H | 2-Cl | 6-NO$_2$ | 3-NO$_2$ | |
| H | 2-Cl | 6-Cl | 3-CH$_2$OCH$_3$ | |
| H | 2-Cl | 6-Cl | 4-SO$_2$CH$_3$ | |
| H | 2-Cl | 6-Cl | 4-NO$_2$ | |
| H | 2-F | 6-F | H | |
| H | 2-F | 6-CH$_3$ | H | |
| H | 2-F | 6-CO$_2$CH$_3$ | H | |
| H | 2-Br | 6-Br | H | |
| H | 2-Br | 6-Br | 4-NO$_2$ | |
| H | 2-Br | 6-CH$_3$ | H | |
| H | 2-NO$_2$ | 6-CH$_3$ | H | |
| H | 2-NO$_2$ | 6-CH$_3$ | 3-CH$_3$ | |
| H | 2-SO$_2$CH$_3$ | 6-CH$_3$ | H | |
| H | 2-SO$_2$C$_2$H$_5$ | 6-CH$_3$ | H | |
| H | 2-SC$_2$H$_5$ | 6-CH$_3$ | H | |
| H | 2-SO$_2$N(CH$_3$)$_2$ | 6-CH$_3$ | H | |
| H | 2-SOC$_2$H$_5$ | 6-CH$_3$ | H | |
| H | 2-OSO$_2$C$_2$H$_5$ | 6-CH$_3$ | H | |
| H | 2-CO$_2$CH$_3$ | 6-CH$_3$ | H | |

TABLE 1-continued

Formula 1

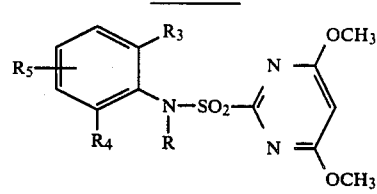

| R | R$_3$ | R$_4$ | R$_5$ | m.p. (°C.) |
|---|---|---|---|---|
| H | 2-CO$_2$C$_2$H$_5$ | 6-CH$_3$ | H | |
| H | 2-COCH$_3$ | 6-CH$_3$ | H | |
| H | 2-COC$_2$H$_5$ | 6-CH$_3$ | H | |
| H | 2-CH$_3$ | 6-CH$_3$ | H | |
| H | 2-OCH$_3$ | 6-OCH$_3$ | H | |

TABLE 2

Formula 2

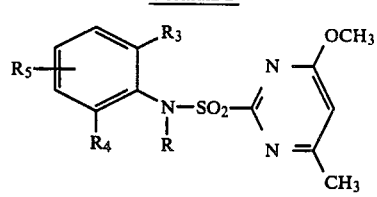

| R | R$_3$ | R$_4$ | R$_5$ | m.p. (°C.) |
|---|---|---|---|---|
| H | 2-Cl | 6-Cl | H | 172-180 |
| H | 2-Cl | 6-Cl | 3-CH$_3$ | |
| H | 2-Cl | 6-Cl | 3-Cl | |
| H | 2-Cl | 6-COOCH$_3$ | H | |
| H | 2-Cl | 6-Br | H | |
| H | 2-Cl | 6-CH$_3$ | H | |
| H | 2-Cl | 6-CH$_2$OCH$_3$ | H | |
| H | 2-Cl | 6-CH$_2$F | H | |
| H | 2-Cl | 6-F | H | |
| H | 2-Cl | 6-SO$_2$CH$_3$ | H | |
| H | 2-Cl | 6-OSO$_2$CH$_3$ | H | |
| H | 2-Cl | 6-SO$_2$N(CH$_3$)$_2$ | H | |
| H | 2-Cl | 6-SOC$_2$H$_5$ | H | |
| H | 2-Cl | 6-SO$_3$CH$_3$ | H | |
| H | 2-Cl | 6-OCH$_3$ | H | |
| H | 2-Cl | 6-CO$_2$C$_2$H$_5$ | H | |
| H | 2-Cl | 6-NO$_2$ | 3-NO$_2$ | |
| H | 2-Cl | 6-Cl | 3-CH$_2$OCH$_3$ | |
| H | 2-Cl | 6-Cl | 4-SO$_2$CH$_3$ | |
| H | 2-Cl | 6-Cl | 4-NO$_2$ | |
| H | 2-F | 6-F | H | |
| H | 2-F | 6-CH$_3$ | H | |
| H | 2-F | 6-CO$_2$CH$_3$ | H | |
| H | 2-Br | 6-Br | H | |
| H | 2-Br | 6-Br | 4-NO$_2$ | |
| H | 2-Br | 6-CH$_3$ | H | |
| H | 2-NO$_2$ | 6-CH$_3$ | H | |
| H | 2-NO$_2$ | 6-CH$_3$ | 3-CH$_3$ | |
| H | 2-SO$_2$CH$_3$ | 6-CH$_3$ | H | |
| H | 2-SO$_2$C$_2$H$_5$ | 6-CH$_3$ | H | |
| H | 2-SC$_2$H$_5$ | 6-CH$_3$ | H | |
| H | 2-SO$_2$N(CH$_3$)$_2$ | 6-CH$_3$ | H | |
| H | 2-SOC$_2$H$_5$ | 6-CH$_3$ | H | |
| H | 2-OSO$_2$C$_2$H$_5$ | 6-CH$_3$ | H | |
| H | 2-CO$_2$CH$_3$ | 6-CH$_3$ | H | |
| H | 2-CO$_2$C$_2$H$_5$ | 6-CH$_3$ | H | |
| H | 2-COCH$_3$ | 6-CH$_3$ | H | |
| H | 2-COC$_2$H$_5$ | 6-CH$_3$ | H | |
| H | 2-CH$_3$ | 6-CH$_3$ | H | |
| H | 2-OCH$_3$ | 6-OCH$_3$ | H | |

TABLE 3

Formula 3

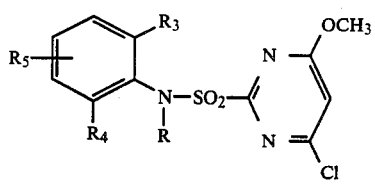

| R | R₃ | R₄ | R₅ | m.p. (°C.) |
|---|----|----|----|------------|
| H | 2-Cl | 6-Cl | H | |
| H | 2-Cl | 6-Cl | 3-CH₃ | |
| H | 2-Cl | 6-Cl | 3-Cl | |
| H | 2-Cl | 6-COOCH₃ | H | |
| H | 2-Cl | 6-Br | H | |
| H | 2-Cl | 6-CH₃ | H | |
| H | 2-Cl | 6-CH₂OCH₃ | H | |
| H | 2-Cl | 6-CH₂F | H | |
| H | 2-Cl | 6-F | H | |
| H | 2-Cl | 6-SO₂CH₃ | H | |
| H | 2-Cl | 6-OSO₂CH₃ | H | |
| H | 2-Cl | 6-SO₂N(CH₃)₂ | H | |
| H | 2-Cl | 6-SOC₂H₅ | H | |
| H | 2-Cl | 6-OCH₃ | H | |
| H | 2-Cl | 6-CO₂C₂H₅ | H | |
| H | 2-Cl | 6-NO₂ | 3-NO₂ | |
| H | 2-Cl | 6-Cl | 3-CH₂OCH₃ | |
| H | 2-Cl | 6-Cl | 4-SO₂CH₃ | |
| H | 2-Cl | 6-Cl | 4-NO₂ | |
| H | 2-F | 6-F | H | |

TABLE 3-continued

Formula 3

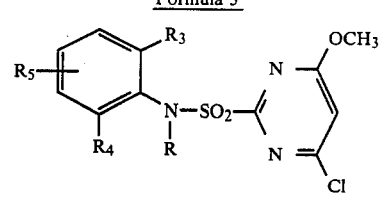

| R | R₃ | R₄ | R₅ | m.p. (°C.) |
|---|----|----|----|------------|
| H | 2-F | 6-CH₃ | H | |
| H | 2-F | 6-CO₂CH₃ | H | |
| H | 2-Br | 6-Br | H | |
| H | 2-Br | 6-Br | 4-NO₂ | |
| H | 2-Br | 6-CH₃ | H | |
| H | 2-NO₂ | 6-CH₃ | H | |
| H | 2-NO₂ | 6-CH₃ | 3-CH₃ | |
| H | 2-SO₂CH₃ | 6-CH₃ | H | |
| H | 2-SO₂C₂H₅ | 6-CH₃ | H | |
| H | 2-SC₂H₅ | 6-CH₃ | H | |
| H | 2-SO₂N(CH₃)₂ | 6-CH₃ | H | |
| H | 2-SOC₂H₅ | 6-CH₃ | H | |
| H | 2-OSO₂C₂H₅ | 6-CH₃ | H | |
| H | 2-CO₂CH₃ | 6-CH₃ | H | |
| H | 2-CO₂C₂H₅ | 6-CH₃ | H | |
| H | 2-COCH₃ | 6-CH₃ | H | |
| H | 2-COC₂H₅ | 6-CH₃ | H | |
| H | 2-CH₃ | 6-CH₃ | H | |
| H | 2-OCH₃ | 6-OCH₃ | H | |

TABLE 4

Formula 4

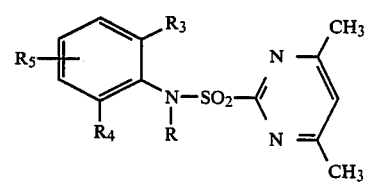

| R | R₃ | R₄ | R₅ | m.p. (°C.) |
|---|----|----|----|------------|
| H | 2-Cl | 6-Cl | H | 261–263 |
| H | 2-Cl | 6-Cl | 3-CH₃ | 234–235 |
| H | 2-Cl | 6-Cl | 3-Cl | |
| H | 2-Cl | 6-COOCH₃ | H | |
| H | 2-Cl | 6-Br | H | |
| H | 2-Cl | 6-CH₃ | H | 215–219 |
| H | 2-Cl | 6-CH₂OCH₃ | H | |
| H | 2-Cl | 6-CH₂F | H | |
| H | 2-Cl | 6-F | H | |
| H | 2-Cl | 6-SO₂CH₃ | H | |
| H | 2-Cl | 6-OSO₂CH₃ | H | |
| H | 2-Cl | 6-SO₂N(CH₃)₂ | H | |
| H | 2-Cl | 6-SOC₂H₅ | H | |
| H | 2-Cl | 6-OCH₃ | H | |
| H | 2-Cl | 6-CO₂C₂H₅ | H | |
| H | 2-Cl | 6-NO₂ | 3-NO₂ | |
| H | 2-Cl | 6-Cl | 3-CH₂OCH₃ | |
| H | 2-Cl | 6-Cl | 4-SO₂CH₃ | |
| H | 2-Cl | 6-Cl | 4-NO₂ | |
| H | 2-F | 6-F | H | 234–239 |
| H | 2-F | 6-CH₃ | H | |
| H | 2-F | 6-CO₂CH₃ | H | |
| H | 2-Br | 6-Br | H | 221–230 |
| H | 2-Br | 6-Br | 4-NO₂ | |
| H | 2-Br | 6-CH₃ | H | |
| H | 2-NO₂ | 6-CH₃ | H | 180–200 |
| H | 2-NO₂ | 6-CH₃ | 3-CH₃ | |
| H | 2-SO₂CH₃ | 6-CH₃ | H | |
| H | 2-SO₂C₂H₅ | 6-CH₃ | H | |
| H | 2-SC₂H₅ | 6-CH₃ | H | |
| H | 2-SO₂N(CH₃)₂ | 6-CH₃ | H | |
| H | 2-SOC₂H₅ | 6-CH₃ | H | |
| H | 2-OSO₂C₂H₅ | 6-CH₃ | H | |
| H | 2-CO₂CH₃ | 6-CH₃ | H | 174–175 |
| H | 2-CO₂CH₃ | Cl | H | |

TABLE 4-continued

Formula 4

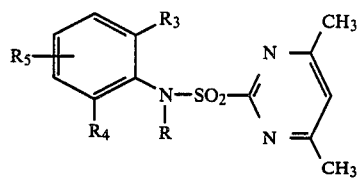

| R | R₃ | R₄ | R₅ | m.p. (°C.) |
|---|----|----|----|------------|
| H | 2-CO₂C₂H₅ | 6-CH₃ | H | |
| H | 2-COCH₃ | 6-CH₃ | H | |
| H | 2-COC₂H₅ | 6-CH₃ | H | |
| H | 2-CH₃ | 6-CH₃ | H | |
| H | 2-OCH₃ | 6-OCH₃ | H | |
| COCH₃ | 2-Cl | 6-Cl | H | |
| CO₂CH₃ | 2-Cl | 6-Cl | 3-CH₃ | |
| CON(CH₃)₂ | 2-Cl | 6-Cl | 3-Cl | |
| CONHCH₃ | 2-Cl | 6-COOCH₃ | H | |
| CSN(CH₃)₂ | 2-Cl | 6-Br | H | |
| CH₂CH=CH₂ | 2-Cl | 6-CH₃ | H | |
| CH₂C≡CH | 2-Cl | 6-CH₂OCH₃ | H | |
| CO₂C₂H₅ | 2-Cl | 6-F | H | |
| CONHPh | 2-Cl | 6-SO₂CH₃ | H | |
| COCH₂Cl | 2-Cl | 6-OSO₂CH₃ | H | |
| COCH₂OCH₃ | 2-Cl | 6-SO₂N(CH₃)₂ | H | |
| COCH₂Cl | 2-Cl | 6-Cl | H | 141–143 |
| H | (1-methyl-5-methyl-tetrazolyl) | CH₃ | H | 205 |
| H | (1-methyl-5-methyl-tetrazolyl) | Cl | H | |
| H | (dimethyl-oxadiazolyl) | CH₃ | H | |
| H | (methyl-oxazolyl) | Cl | H | |
| H | (methyl-tetrazolyl) | Cl | H | |
| H | (thienyl) | Cl | H | |
| H | (4-methyl-5-oxo-tetrazolinyl) | Cl | H | |

TABLE 4-continued

Formula 4

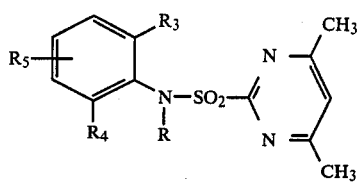

| R | R₃ | R₄ | R₅ | m.p. (°C.) |
|---|---|---|---|---|
| H | CH₃ 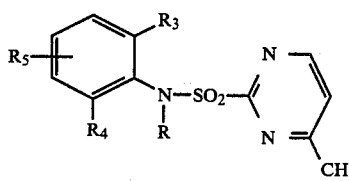 | Cl | H | |
| H | CH₃ 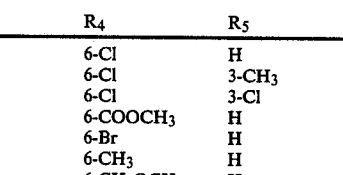 | Cl | H | |

TABLE 5

Formula 5

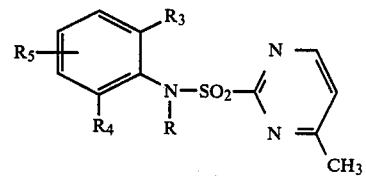

| R | R₃ | R₄ | R₅ | m.p. (°C.) |
|---|---|---|---|---|
| H | 2-Cl | 6-Cl | H | 167–168 |
| H | 2-Cl | 6-Cl | 3-CH₃ | |
| H | 2-Cl | 6-Cl | 3-Cl | |
| H | 2-Cl | 6-COOCH₃ | H | |
| H | 2-Cl | 6-Br | H | |
| H | 2-Cl | 6-CH₃ | H | |
| H | 2-Cl | 6-CH₂OCH₃ | H | |
| H | 2-Cl | 6-CH₂F | H | |
| H | 2-Cl | 6-F | H | |
| H | 2-Cl | 6-SO₂CH₃ | H | |
| H | 2-Cl | 6-OSO₂CH₃ | H | |
| H | 2-Cl | 6-SO₂N(CH₃)₂ | H | |
| H | 2-Cl | 6-SOC₂H₅ | H | |
| H | 2-Cl | 6-OCH₃ | H | |
| H | 2-Cl | 6-CO₂C₂H₅ | H | |
| H | 2-Cl | 6-NO₂ | 3-NO₂ | |
| H | 2-Cl | 6-Cl | 3-CH₂OCH₃ | |
| H | 2-Cl | 6-Cl | 4-SO₂CH₃ | |
| H | 2-Cl | 6-Cl | 4-NO₂ | |
| H | 2-F | 6-F | H | 171–180 |
| H | 2-F | 6-CH₃ | H | |
| H | 2-F | 6-CO₂CH₃ | H | |
| H | 2-Br | 6-Br | H | 198–204 |
| H | 2-Br | 6-Br | 4-NO₂ | |
| H | 2-Br | 6-CH₃ | H | |
| H | 2-NO₂ | 6-CH₃ | H | |
| H | 2-NO₂ | 6-CH₃ | 3-CH₃ | |
| H | 2-SO₂CH₃ | 6-CH₃ | H | |
| H | 2-SO₂C₂H₅ | 6-CH₃ | H | |
| H | 2-SC₂H₅ | 6-CH₃ | H | |
| H | 2-SO₂N(CH₃)₂ | 6-CH₃ | H | |
| H | 2-SOC₂H₅ | 6-CH₃ | H | |
| H | 2-OSO₂C₂H₅ | 6-CH₃ | H | |
| H | 2-CO₂CH₃ | 6-CH₃ | H | |
| H | 2-CO₂C₂H₅ | 6-CH₃ | H | |
| H | 2-COCH₃ | 6-CH₃ | H | |
| H | 2-COC₂H₅ | 6-CH₃ | H | |
| H | 2-CH₃ | 6-CH₃ | H | |

TABLE 5-continued

Formula 5

| R | R₃ | R₄ | R₅ | m.p. (°C.) |
|---|---|---|---|---|
| H | 2-OCH₃ | 6-OCH₃ | H | |

TABLE 6

Formula 6

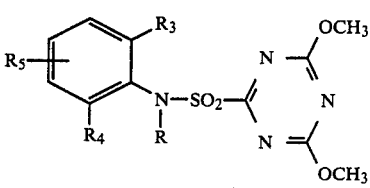

| R | R₃ | R₄ | R₅ | m.p. (°C.) |
|---|---|---|---|---|
| H | 2-Cl | 6-Cl | H | |
| H | 2-Cl | 6-Cl | 3-CH₃ | |
| H | 2-Cl | 6-Cl | 3-Cl | |
| H | 2-Cl | 6-COOCH₃ | H | |
| H | 2-Cl | 6-Br | H | |
| H | 2-Cl | 6-CH₃ | H | |
| H | 2-Cl | 6-CH₂OCH₃ | H | |
| H | 2-Cl | 6-CH₂F | H | |
| H | 2-Cl | 6-F | H | |
| H | 2-Cl | 6-SO₂CH₃ | H | |
| H | 2-Cl | 6-OSO₂CH₃ | H | |
| H | 2-Cl | 6-SO₂N(CH₃)₂ | H | |
| H | 2-Cl | 6-SOC₂H₅ | H | |
| H | 2-Cl | 6-OCH₃ | H | |
| H | 2-Cl | 6-CO₂C₂H₅ | H | |
| H | 2-Cl | 6-NO₂ | 3-NO₂ | |
| H | 2-Cl | 6-Cl | 3-CH₂OCH₃ | |
| H | 2-Cl | 6-Cl | 4-SO₂CH₃ | |
| H | 2-Cl | 6-Cl | 4-NO₂ | |
| H | 2-F | 6-F | H | |
| H | 2-F | 6-CH₃ | H | |

TABLE 6-continued

Formula 6

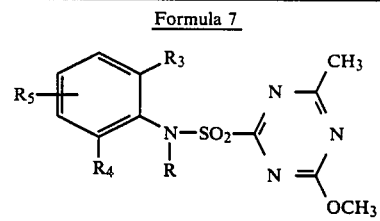

| R | R₃ | R₄ | R₅ | m.p. (°C.) |
|---|---|---|---|---|
| H | 2-F | 6-CO₂CH₃ | H | |
| H | 2-Br | 6-Br | H | |
| H | 2-Br | 6-Br | 4-NO₂ | |
| H | 2-Br | 6-CH₃ | H | |
| H | 2-NO₂ | 6-CH₃ | H | |
| H | 2-NO₂ | 6-CH₃ | 3-CH₃ | |
| H | 2-SO₂CH₃ | 6-CH₃ | H | |
| H | 2-SO₂C₂H₅ | 6-CH₃ | H | |
| H | 2-SC₂H₅ | 6-CH₃ | H | |
| H | 2-SO₂N(CH₃)₂ | 6-CH₃ | H | |
| H | 2-SOC₂H₅ | 6-CH₃ | H | |
| H | 2-OSO₂C₂H₅ | 6-CH₃ | H | |
| H | 2-CO₂CH₃ | 6-CH₃ | H | |
| H | 2-CO₂C₂H₅ | 6-CH₃ | H | |
| H | 2-COCH₃ | 6-CH₃ | H | |
| H | 2-COC₂H₅ | 6-CH₃ | H | |
| H | 2-CH₃ | 6-CH₃ | H | |
| H | 2-OCH₃ | 6-OCH₃ | H | |

TABLE 7

Formula 7

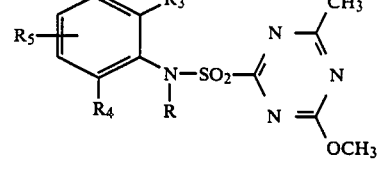

| R | R₃ | R₄ | R₅ | m.p. (°C.) |
|---|---|---|---|---|
| H | 2-Cl | 6-Cl | H | |
| H | 2-Cl | 6-Cl | 3-CH₃ | |
| H | 2-Cl | 6-Cl | 3-Cl | |
| H | 2-Cl | 6-COOCH₃ | H | |
| H | 2-Cl | 6-Br | H | |
| H | 2-Cl | 6-CH₃ | H | |
| H | 2-Cl | 6-CH₂OCH₃ | H | |
| H | 2-Cl | 6-CH₂F | H | |
| H | 2-Cl | 6-F | H | |
| H | 2-Cl | 6-SO₂CH₃ | H | |
| H | 2-Cl | 6-OSO₂CH₃ | H | |
| H | 2-Cl | 6-SO₂N(CH₃)₂ | H | |
| H | 2-Cl | 6-SOC₂H₅ | H | |
| H | 2-Cl | 6-OCH₃ | H | |
| H | 2-Cl | 6-CO₂C₂H₅ | H | |
| H | 2-Cl | 6-NO₂ | 3-NO₂ | |
| H | 2-Cl | 6-Cl | 3-CH₂OCH₃ | |
| H | 2-Cl | 6-Cl | 4-SO₂CH₃ | |
| H | 2-Cl | 6-Cl | 4-NO₂ | |
| H | 2-F | 6-F | H | |
| H | 2-F | 6-CH₃ | H | |
| H | 2-F | 6-CO₂CH₃ | H | |
| H | 2-Br | 6-Br | H | |
| H | 2-Br | 6-Br | 4-NO₂ | |
| H | 2-Br | 6-CH₃ | H | |
| H | 2-NO₂ | 6-CH₃ | H | |
| H | 2-NO₂ | 6-CH₃ | 3-CH₃ | |
| H | 2-SO₂CH₃ | 6-CH₃ | H | |
| H | 2-SO₂C₂H₅ | 6-CH₃ | H | |
| H | 2-SC₂H₅ | 6-CH₃ | H | |
| H | 2-SO₂N(CH₃)₂ | 6-CH₃ | H | |
| H | 2-SOC₂H₅ | 6-CH₃ | H | |
| H | 2-OSO₂C₂H₅ | 6-CH₃ | H | |
| H | 2-CO₂CH₃ | 6-CH₃ | H | |
| H | 2-CO₂C₂H₅ | 6-CH₃ | H | |

TABLE 7-continued

Formula 7

| R | R₃ | R₄ | R₅ | m.p. (°C.) |
|---|---|---|---|---|
| H | 2-COCH₃ | 6-CH₃ | H | |
| H | 2-COC₂H₅ | 6-CH₃ | H | |
| H | 2-CH₃ | 6-CH₃ | H | |
| H | 2-OCH₃ | 6-OCH₃ | H | |

TABLE 8

Formula 8

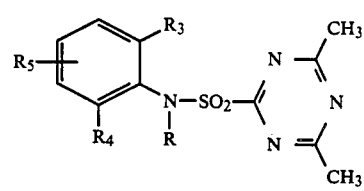

| R | R₃ | R₄ | R₅ | m.p. (°C.) |
|---|---|---|---|---|
| H | 2-Cl | 6-Cl | H | |
| H | 2-Cl | 6-Cl | 3-CH₃ | |
| H | 2-Cl | 6-Cl | 3-Cl | |
| H | 2-Cl | 6-COOCH₃ | H | |
| H | 2-Cl | 6-Br | H | |
| H | 2-Cl | 6-CH₃ | H | |
| H | 2-Cl | 6-CH₂OCH₃ | H | |
| H | 2-Cl | 6-CH₂F | H | |
| H | 2-Cl | 6-F | H | |
| H | 2-Cl | 6-SO₂CH₃ | H | |
| H | 2-Cl | 6-OSO₂CH₃ | H | |
| H | 2-Cl | 6-SO₂N(CH₃)₂ | H | |
| H | 2-Cl | 6-SOC₂H₅ | H | |
| H | 2-Cl | 6-OCH₃ | H | |
| H | 2-Cl | 6-CO₂C₂H₅ | H | |
| H | 2-Cl | 6-NO₂ | 3-NO₂ | |
| H | 2-Cl | 6-Cl | 3-CH₂OCH₃ | |
| H | 2-Cl | 6-Cl | 4-SO₂CH₃ | |
| H | 2-Cl | 6-Cl | 4-NO₂ | |
| H | 2-F | 6-F | H | |
| H | 2-F | 6-CH₃ | H | |
| H | 2-F | 6-CO₂CH₃ | H | |
| H | 2-Br | 6-Br | H | |
| H | 2-Br | 6-Br | 4-NO₂ | |
| H | 2-Br | 6-CH₃ | H | |
| H | 2-NO₂ | 6-CH₃ | H | |
| H | 2-NO₂ | 6-CH₃ | 3-CH₃ | |
| H | 2-SO₂CH₃ | 6-CH₃ | H | |
| H | 2-SO₂C₂H₅ | 6-CH₃ | H | |
| H | 2-SC₂H₅ | 6-CH₃ | H | |
| H | 2-SO₂N(CH₃)₂ | 6-CH₃ | H | |
| H | 2-SOC₂H₅ | 6-CH₃ | H | |
| H | 2-OSO₂C₂H₅ | 6-CH₃ | H | |
| H | 2-CO₂CH₃ | 6-CH₃ | H | |
| H | 2-CO₂C₂H₅ | 6-CH₃ | H | |
| H | 2-COCH₃ | 6-CH₃ | H | |
| H | 2-COC₂H₅ | 6-CH₃ | H | |
| H | 2-CH₃ | 6-CH₃ | H | |
| H | 2-OCH₃ | 6-OCH₃ | H | |

TABLE 9

Formula 9

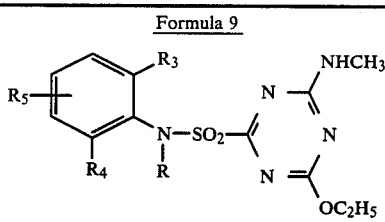

| R | R₃ | R₄ | R₅ | m.p. (°C.) |
|---|---|---|---|---|
| H | 2-Cl | 6-Cl | H | |
| H | 2-Cl | 6-Cl | 3-CH₃ | |
| H | 2-Cl | 6-Cl | 3-Cl | |
| H | 2-Cl | 6-COOCH₃ | H | |
| H | 2-Cl | 6-Br | H | |
| H | 2-Cl | 6-CH₃ | H | |
| H | 2-Cl | 6-CH₂OCH₃ | H | |
| H | 2-Cl | 6-CH₂F | H | |
| H | 2-Cl | 6-F | H | |
| H | 2-Cl | 6-SO₂CH₃ | H | |
| H | 2-Cl | 6-OSO₂CH₃ | H | |
| H | 2-Cl | 6-SO₂N(CH₃)₂ | H | |
| H | 2-Cl | 6-SOC₂H₅ | H | |
| H | 2-Cl | 6-OCH₃ | H | |
| H | 2-Cl | 6-CO₂C₂H₅ | H | |
| H | 2-Cl | 6-NO₂ | 3-NO₂ | |
| H | 2-Cl | 6-Cl | 3-CH₂OCH₃ | |
| H | 2-Cl | 6-Cl | 4-SO₂CH₃ | |
| H | 2-Cl | 6-Cl | 4-NO₂ | |
| H | 2-F | 6-F | H | |
| H | 2-F | 6-CH₃ | H | |
| H | 2-F | 6-CO₂CH₃ | H | |
| H | 2-Br | 6-Br | H | |
| H | 2-Br | 6-Br | 4-NO₂ | |
| H | 2-Br | 6-CH₃ | H | |
| H | 2-NO₂ | 6-CH₃ | H | |
| H | 2-NO₂ | 6-CH₃ | 3-CH₃ | |
| H | 2-SO₂CH₃ | 6-CH₃ | H | |
| H | 2-SO₂C₂H₅ | 6-CH₃ | H | |
| H | 2-SC₂H₅ | 6-CH₃ | H | |
| H | 2-SO₂N(CH₃)₂ | 6-CH₃ | H | |
| H | 2-SOC₂H₅ | 6-CH₃ | H | |
| H | 2-OSO₂C₂H₅ | 6-CH₃ | H | |
| H | 2-CO₂CH₃ | 6-CH₃ | H | |
| H | 2-CO₂C₂H₅ | 6-CH₃ | H | |
| H | 2-COCH₃ | 6-CH₃ | H | |
| H | 2-COC₂H₅ | 6-CH₃ | H | |
| H | 2-CH₃ | 6-CH₃ | H | |
| H | 2-OCH₃ | 6-OCH₃ | H | |

TABLE 10

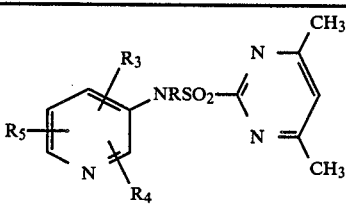

Formula 10

| R | R₃ | R₄ | R₅ | m.p. (°C.) |
|---|---|---|---|---|
| H | 2-Cl | 4-CH₃ | H | |
| H | 2-SCH₃ | 4-CH₃ | H | |
| H | 2-SOCH₃ | 4-CH₃ | H | |
| H | 2-SO₂CH₃ | 4-CH₃ | H | |
| H | 2-CO₂CH₃ | 4-CH₃ | H | |
| H | 2-OCH₃ | 4-CH₃ | H | |
| H | 2-CO₂C₂H₅ | 4-CH₃ | H | |
| H | 2-NO₂ | 4-CH₃ | H | |
| H | 2-SO₂N(CH₃)₂ | 4-CH₃ | H | |
| H | 2-CH₃ | 4-CH₃ | H | |
| H | 2-Cl | 4-CO₂CH₃ | H | |
| H | 2-Cl | 4-Cl | H | |
| H | 2-Cl | 4-SCH₃ | H | |
| H | 2-Cl | 4-SO₂CH₃ | H | |
| H | 2-CH₃ | 4-NO₂ | H | |

TABLE 10-continued

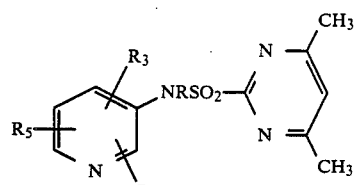

Formula 10

| R | R₃ | R₄ | R₅ | m.p. (°C.) |
|---|---|---|---|---|
| H | 2-CH₃ | 4-SO₂N(CH₃)₂ | H | |
| H | 2-Cl | 4-COCH₃ | H | |

TABLE 11

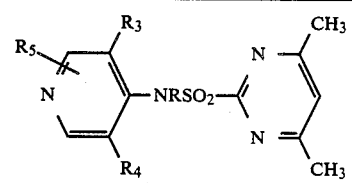

Formula 11

| R | R₃ | R₄ | R₅ | m.p. (°C.) |
|---|---|---|---|---|
| H | Cl | Cl | H | 176–180 |
| H | Cl | CH₃ | H | |
| H | Cl | CO₂CH₃ | H | |
| H | SCH₃ | CH₃ | H | |
| H | SO₂CH₃ | CH₃ | H | |
| H | CO₂CH₃ | CH₃ | H | |
| H | NO₂ | CH₃ | H | |

TABLE 12

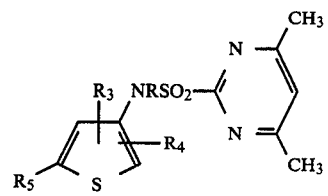

Formula 12

| R | R₃ | R₄ | R₅ | m.p. (°C.) |
|---|---|---|---|---|
| H | 2-CO₂CH₃ | 4-CH₃ | H | 173–174 |
| H | 2-CO₂CH₃ | 4-Br | H | |
| H | 2-SCH₃ | 4-CH₃ | H | |
| H | 2-SO₂CH₃ | 4-CH₃ | H | |
| H | 2-COCH₃ | 4-CH₃ | H | |
| H | 2-COC₂H₅ | 4-CH₃ | H | |
| H | 2-CH₂OCH₃ | 4-CH₃ | H | |
| H | 2-NO₂ | 4-CH₃ | H | |
| H | 2-Cl | 4-CH₃ | H | |
| H | 2-Br | 4-CH₃ | H | |
| H | 4-Br | 2-CH₃ | H | |
| H | 4-SO₂CH₃ | 2-Cl | H | |
| H | 4-SO₂CH₃ | 2-CH₃ | H | |
| H | 2-SO₂N(CH₃)₂ | 4-CH₃ | H | |
| H | 2-SO₂N(CH₃)₂ | 4-Cl | H | |
| H | 2-OSO₂CH₃ | 4-Cl | H | |

TABLE 13

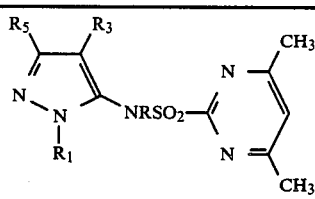

Formula 13

| R | R₂' | R₃ | R₅ | m.p. (°C.) |
|---|---|---|---|---|
| H | CH₃ | 4-CO₂CH₃ | 3-CH₃ | |
| H | CH₃ | 4-CO₂CH₃ | H | 137 |
| H | CH₃ | 4-CO₂C₂H₅ | 3-CH₃ | |
| H | CH₃ | 4-CO₂C₂H₅ | H | 143–145 |
| H | CH₃ | 4-Cl | H | |
| H | CH₃ | 4-Cl | 3-CH₃ | |
| H | CH₃ | 4-SO₂CH₃ | H | |
| H | CH₃ | 4-SO₂CH₃ | 3-CH₃ | |
| H | CH₃ | 4-SO₂N(CH₃)₂ | H | |
| H | CH₃ | 4-SO₂N(CH₃)₂ | 3-CH₃ | |

TABLE 14

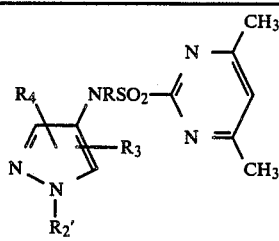

Formula 14

| R | R₂' | R₃ | R₅ | m.p. (°C.) |
|---|---|---|---|---|
| H | CH₃ | 3-Cl | H | |
| H | CH₃ | 3-CO₂CH₃ | 5-CH₃ | |
| H | CH₃ | 3-CO₂C₂H₅ | H | |
| H | CH₃ | 3-COCH₃ | H | |
| H | CH₃ | 3-COCH₃ | 5-CH₃ | |
| H | CH₃ | 3-SO₂CH₃ | H | |
| H | CH₃ | 3-SO₂CH₃ | 5-CH₃ | |

TABLE 15

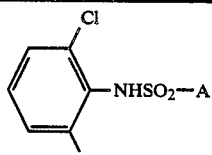

Formula 15

| A | X₁ | Y₁ | m.p. (°C.) |
|---|---|---|---|
| A-2 | OCH₃ | O | |
| A-2 | CH₃ | O | |
| A-2 | Cl | O | |
| A-2 | OCH₃ | CH₂ | |

Formula 16

| A | X₁ | Y₃ | m.p. (°C.) |
|---|---|---|---|
| A-4 | OCH₃ | CH₃ | |
| A-4 | CH₃ | CH₃ | |
| A-4 | OCH₃ | H | |
| A-4 | OC₂H₅ | H | |

Formula 17

| A | X₁ | m.p. (°C.) |
|---|---|---|
| A-3 | CH₃ | |
| A-3 | OCH₃ | |
| A-3 | Cl | |
| A-3 | OC₂H₅ | |

Formula 18

TABLE 15-continued

| A | X₂ | Y₂ | m.p. (°C.) |
|---|---|---|---|
| A-5 | CH₃ | OCH₃ | |
| A-5 | CH₃ | CH₃ | |
| A-5 | CH₃ | Cl | |
| A-5 | C₂H₅ | OCH₃ | |

Formula 19

| A | X₃ | m.p. (°C.) |
|---|---|---|
| A-6 | CH₃ | |
| A-6 | OCH₃ | |

Formula 20

| A | X₁ | Y₂ | m.p. (°C.) |
|---|---|---|---|
| A-7 | OCH₃ | OCH₃ | |
| A-7 | OCH₃ | CH₃ | |

Formula 21

| A | X₁ | Y₂ | X₄ | m.p. (°C.) |
|---|---|---|---|---|
| A-8 | OCH₃ | OCH₃ | CH₃ | |
| A-8 | CH₃ | OCH₃ | CH₃ | |
| A-8 | Cl | Cl | CH₃ | |
| A-8 | Cl | OCH₃ | CH₃ | |

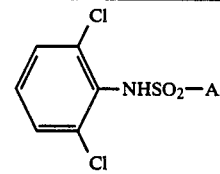

| A | X | Y | Z | m.p. (°C.) |
|---|---|---|---|---|
| A-1 | CH₃ | OCF₂H | CH | |
| A-1 | CH₃ | SCH₃ | CH | |
| A-1 | CH₃ | S(CH₂)₂Cl | CH | |
| A-1 | CH₃ | CH₂OCH₃ | CH | |
| A-1 | CH₃ | O(CH₂)₂OCH₃ | CH | |
| A-1 | CH₃ | NH₂ | CH | |
| A-1 | CH₃ | N(CH₃)₂ | CH | |
| A-1 | CH₃ | NHCH₃ | CH | |
| A-1 | CH₃ | OCH₂CH=CH₂ | CH | |
| A-1 | CH₃ | OCH₂C≡CH | CH | |
| A-1 | CH₃ | CH₂SCH₃ | CH | |
| A-1 | CH₃ | CH₂S(O)CH₃ | CH | |
| A-1 | CH₃ | CH₂S(O)₂CH₃ | CH | |
| A-1 | CH₃ | CF₃ | CH | |
| A-1 | CH₃ | N₃ | CH | |
| A-1 | CH₃ | C≡CH | CH | |
| A-1 | CH₃ | C≡N | CH | |
| A-1 | CH₃ | CHO | CH | |
| A-1 | CH₃ | N(OCH₃)CH₃ | CH | |
| A-1 | OCH₃ | CH₂CH₃ | CH | |
| A-1 | Cl | OCH₃ | CH | |
| A-1 | CH₃ | SCH₃ | N | |
| A-1 | cyclopropyl | CH₃ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 16

|  | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are some times desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

Example 5
Wettable Powder

| | |
|---|---|
| N—(2,6-dichloro-3-methylphenyl)-4,6-dimethyl-2-pyrimidinesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

Example 6
Wettable Powder

| | |
|---|---|
| N—(2-chloro-6-methylphenyl)-4,6-dimethyl-2-pyrimdinesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

Example 7
Granule

| | |
|---|---|
| Wettable powder of Example 6 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

Example 8
Extruded Pellet

| | |
|---|---|
| N—(2,6-dichloro-3-methylphenyl)-4,6-dimethyl-2-pyrimidinesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

Example 9
Oil Suspension

| | |
|---|---|
| N—(2,6-dichloro-3-methylphenyl)-4,6-dimethyl-2-pyrimidinesulfonamide | 25% |
| polyoxyethylene sorbitol hexaoleate | 5% |

Example 9
Oil Suspension

| | |
|---|---|
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

Example 10
Wettable Powder

| | |
|---|---|
| N—(2,6-dichloro-3-methylphenyl)-4,6-dimethyl-2-pyrimidinesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Example 11
Low Strength Granule

| | |
|---|---|
| N—(2,6-dichlorophenyl)-4,6-dimethyl-2-pyrimidinesulfonamide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

Example 12
Aqueous Suspension

| | |
|---|---|
| N—(2,6-dichlorophenyl)-4,6-dimethoxy-2-pyrimidinesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

Example 13
Solution

| | |
|---|---|
| N—(2,6-dichloro-3-methylphenyl)-4,6-dimethyl-2-pyrimidinesulfonamide | 5% |
| water | 95% |

The salt is added directly to the water with stirring to produce the solution, which may then be packaged for use.

Example 14
Low Strength Granule

| | |
|---|---|
| N—(2,6-dichlorophenyl)-4,6-dimethyl-2-pyrimidinesulfonamide | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

Example 15
Granule

| | |
|---|---|
| N—(2,6-dichloro-3-methylphenyl)-4,6-dimethyl-2-pyrimidinesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

Example 16
High Strength Concentrate

| | |
|---|---|
| N—(2,6-dichlorophenyl)-4-methoxy-6-methyl-2-pyrimidinesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

Example 17
Wettable Powder

| | |
|---|---|
| N—(2,6-dichlorophenyl)-4-methoxy-6-methyl-2-pyrimidinesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is shifted through a U.S.S. No. 50 screen and then packaged.

Example 18
Wettable Powder

| | |
|---|---|
| N—(2,6-dichlorophenyl)-4,6-dimethyl-2-pyrimidinesulfonamide | 40% |

Example 18
Wettable Powder

| | |
|---|---|
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

Example 19
Oil Suspension

| | |
|---|---|
| N—(2,6-dichlorophenyl)-4,6-dimethoxy-2-pyrimidinesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Example 20
Dust

| | |
|---|---|
| N—(2-chloro-6-methylphenyl)-4,6-dimethyl-2-pyrimidinesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Example 21
Emulsifiable Concentrate

| | |
|---|---|
| N—(2,6-dichloro-3-methylphenyl)-4,6-dimethyl-2-pyrimidinesulfonamide | 10% |
| chlorobenzene | 84% |
| sorbitan monostearate and polyoxyethylene condensates thereof | 6% |

The ingredients are combined and stirred to produce a solution which can be emulsified in water for application.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in-theaters, around billboards, highway and railroad structures. Some of the compounds have utility for selective weed control in crops such as rice, wheat, barley, soybeans and corn. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.004 to 10 kg/ha, the lower rates being suggested for use on lighter soils and/or those having a low organic matter content, for plant growth modification or for situations where only short-term persistence is required, such as a herbicide for fallow land.

The compounds of the invention may be used in combination with any other commercial herbicide, non-limiting examples of which are those of the triazine, triazole, uracil, urea, amide, diphenyl ether, carbamate, imidazolinone, cineole and bipyridylium types.

The herbicidal properties of the subject compounds were discovered in a number of greenhouse tests. The test procedures and results follow.

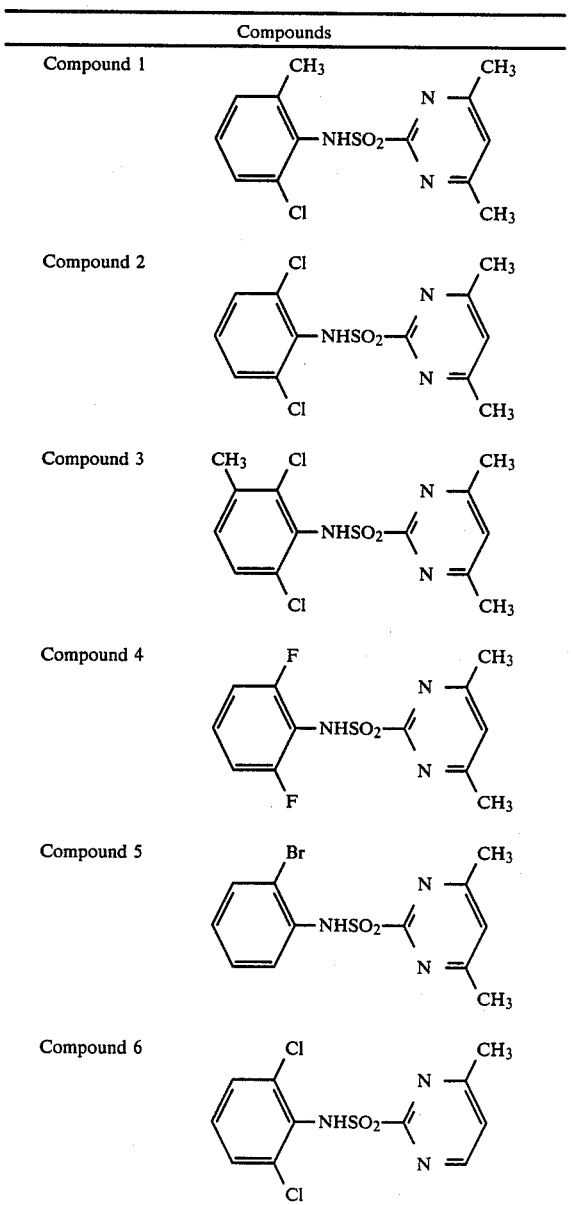

Compounds

Compound 7

Compound 8

Compound 9

Compound 10

Compound 11

Compound 12

Compound 13

Compound 14

Test A

Seeds of crabgrass (Digitaria sp.), barnyardgrass (Echinochloa crusgalli), giant foxtail (Setaria faberi), wild oats (Avena fatua), cheatgrass (Bromus secalinus), velvetleaf (Abutilon theophrasti), morningglory (Ipomoea spp.), cocklebur (Xanthium pennsylvanicum), sorghum, corn, soybean, sugarbeet, cotton, rice, wheat, barley and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

B=burn;
C=chlorosis/necrosis;
D=defoliation;
E=emergence inhibition;
G=growth retardation;
H=formative effect;
U=unusual pigmentation;
X=axillary stimulation;
S=albinism; and
6Y=abscised buds of flowers.

It is noted that Compound 10 exhibits little herbicidal or plant growth regulant activity at an application rate of 0.4 kg/ha; it is thought that this compound would have activity at an application rate not exceeding 10 kg/ha.

TABLE A

| | CMPD 1 | | CMPD 2 | | CMPD 3 | | CMPD 4 | | CMPD 5 | |
|---|---|---|---|---|---|---|---|---|---|---|
| RATE = KG/HA | 0.4 | 2 | 0.4 | 2 | 0.4 | 2 | 0.05 | 0.4 | 0.5 | 0.4 |
| POSTEMERGENCE | | | | | | | | | | |
| COTTON | 3C,7G | 9C | 10C | 10C | 10C | 10C | 0 | 4C,9G | 0 | 10C |
| MORNING GLORY | 2C,5H | 5C,9H | 10C | 10C | 10C | 10C | 2G | 3C,8G | 0 | 10C |
| COCKLEBUR | 2C,6H | 3C,9H | 10C | 10C | 2C,8H | 3C,9H | 0 | 3C,5H | 2H | 9C |
| NUTSEDGE | 7G | 2C,9G | 5C,9G | 9C | 8G | 4C,9G | 0 | 2C,9G | 0 | 10C |
| CRABGRASS | 6G | 3C,8G | 1C,1H | 2C,7G | 0 | 7G | 0 | 0 | 0 | 4G |
| BARNYARD GRASS | 3C,9H | 9H | 3C,9H | 5C,9H | 3G | 3C,6H | 0 | 0 | 0 | 9H |
| WILD OATS | 2C | 2C,9G | 2G | 7G | 0 | 1C | 0 | 0 | 0 | 3C,5G |
| WHEAT | 4G | 9G | 5G | 7G | 0 | 0 | 0 | 0 | 0 | 4G |
| CORN | 2C,5H | 2C,9H | 3C,7H | 9H | 0 | 4G | 0 | 0 | 0 | 7G |
| SOYBEAN | 4C,4H | 5C,9G | 9C | 9C | 9C | 9C | 0 | 2C,5H | 0 | 3C,8G |
| RICE | 4C,9G | 3C,9G | 5C,9G | 4C,9G | 6G | 6G | 0 | 6G | 0 | 8G |

TABLE A-continued

| | | | | | | | | | | |
|---|---|---|---|---|---|---|---|---|---|---|
| SORGHUM | 3C,8G | 3C,9G | 9H | 4C,9H | 2G | 6G | 0 | 2G | 0 | 4C,9H |
| CHEATGRASS | 2C,8G | 3C,6G | 2C,7G | 3C,9G | 6G | 0 | 0 | 0 | 0 | 7G |
| SUGAR BEETS | 3C,8G | 5C,9G | 10C | 10C | 4C,9G | 9C | 0 | 9C | 2C,2G | 9C |
| VELVETLEAF | 2C,6H | 4C,9H | 10C | 10C | 10C | 9C | 1H | 5C,9G | 0 | 10C |
| GIANT FOXTAIL | 2C,8G | 3C,9H | 3C,9G | 5C,9G | 2G | 3G | 0 | 1H | 0 | 6G |
| BARLEY | 5G | 9G | 3C,8G | 9H | 0 | 3G | 0 | 0 | 0 | 3G |

PREEMERGENCE

| | | | | | | | | | | |
|---|---|---|---|---|---|---|---|---|---|---|
| COTTON | 8G | 9G | 9G | 10C | 9G | 9G | 8G | 9G | 2G | 9G |
| MORNING GLORY | 6H | 9G | 9C | 10C | 10C | 10C | 8G | 9G | 3C,8H | 10C |
| COCKLEBUR | 3H | 8H | 8H | 9H | 7H | 9H | 8H | 9H | 3C,8H | 9H |
| NUTSEDGE | 9G | 9G | 10E | 10E | 10E | 10E | 7G | 10E | 10E | 10E |
| CRABGRASS | 5G | 9G | 3G | 2C,7G | 0 | 2G | 0 | 2G | 2G | 3G |
| BARNYARD GRASS | 8H | 9H | 3C,9H | 9H | 7H | 3C,8H | 2H | 3C,8G | 8H | 3C,9H |
| WILD OATS | 3G | 8G | 6G | 8G | 0 | 2G | 0 | 7G | 0 | 6G |
| WHEAT | 4G | 7G | 5G | 8G | 2G | 3G | 0 | 5G | 0 | 5G |
| CORN | 3C,7G | 3C,8H | 3C,9H | 9H | 5G | 3C,7G | 2G | 9H | 3C,9H | 3C,9H |
| SOYBEAN | 4C,4H | 8H | 3C,8H | 3C,9H | 3C,8H | 3C,8H | 2C,7G | 9H | 2C,4H | 3C,7H |
| RICE | 6G | 9H | 8H | 4C,9G | 5G | 6G | 2C,7G | 9H | 4G | 3C,9G |
| SORGHUM | 3C,8G | 3C,9H | 3C,9G | 2C,9H | 5G | 3C,7H | 3C,4G | 3C,9H | 3C,6G | 4C,9H |
| CHEATGRASS | 4G | 8G | 8G | 9G | 6G | 3G | 7G | 8G | 9G | 9G |
| SUGAR BEETS | 9G | 9G | 4C,9G | 5C,9G | 8G | 8G | 4C,9G | 5C,9G | 5C,9G | 5C,9G |
| VELVETLEAF | 3H | 9G | 5C,9G | 9C | 5C,9G | 9C | 8G | 4C,9G | 4C,9G | 9G |
| GIANT FOXTAIL | 3C,6G | 9H | 3C,9H | 3C,9H | 0 | 5G | 0 | 2C,5G | 0 | 7G |
| BARLEY | 5G | 6G | 3C,8G | 2C,9G | 4G | 5G | 0 | 5G | 2G | 3C,8G |

| | CMPD 6 | | CMPD 7 | | CMPD 8 | | CMPD 9 | | CMPD 10 | |
|---|---|---|---|---|---|---|---|---|---|---|
| RATE = KG/HA | 0.05 | 0.4 | 0.05 | 0.4 | 0.05 | 0.4 | 0.05 | 0.4 | 0.05 | 0.4 |

POSTEMERGENCE

| | | | | | | | | | | |
|---|---|---|---|---|---|---|---|---|---|---|
| COTTON | 9C | 9C | 5C,9G | 10C | 10C | 10C | 2G | 3C,9G | 0 | 0 |
| MORNING GLORY | 9C | 10C | 3C,8H | 10C | 10C | 9C | 2G | 3C,7G | 0 | 0 |
| COCKLEBUR | 4C,9G | 10C | 4C,9H | 10C | 5C,9H | 10C | 1H | 3C,8H | 0 | 0 |
| NUTSEDGE | 8G | 9G | 8G | 5C,9G | 9G | 9G | 0 | 3C,8G | 0 | 0 |
| CRABGRASS | 0 | 4G | 0 | 5G | 0 | 6G | 0 | 3C,5G | 0 | 0 |
| BARNYARD GRASS | 2G | 3C,7H | 0 | 7H | 0 | 3C,6H | 0 | 2C,9H | 0 | 0 |
| WILD OATS | 0 | 0 | 0 | 3G | 0 | 0 | 0 | 2C,4G | 0 | 0 |
| WHEAT | 0 | 2G | 0 | 5G | 0 | 0 | 0 | 0 | 0 | 0 |
| CORN | 0 | 0 | 0 | 4G | 0 | 0 | 0 | 7H | 0 | 0 |
| SOYBEAN | 2H | 2C,3H | 2C,2H | 3C,7G | 0 | 2C,5G | 2G | 2H | 0 | 0 |
| RICE | 7G | 4C,9G | 7G | 4C,9G | 7G | 5C,9G | 0 | 8G | 0 | 0 |
| SORGHUM | 4G | 4C,9G | 3G | 4C,9H | 1C | 3C,7G | 0 | 2C,7G | 0 | 0 |
| CHEATGRASS | 0 | 5G | 0 | 2C,5G | 2G | 5G | 0 | 2C,8G | 0 | 0 |
| SUGAR BEETS | 3C,7H | 9C | 4C,9G | 9C | 3C,8G | 9C | 2H | 3C,7H | 0 | 0 |
| VELVETLEAF | 6G | 9C | 8G | 9C | 7G | 9C | 0 | 3C,9G | 0 | 0 |
| GIANT FOXTAIL | 2G | 2C,7G | 2H | 5H | 2G | 3C,8G | 0 | 2C,9G | 0 | 0 |
| BARLEY | 0 | 2C,6G | 0 | 3G | 2G | 6G | 0 | 3G | 0 | 0 |

PREEMERGENCE

| | | | | | | | | | | |
|---|---|---|---|---|---|---|---|---|---|---|
| COTTON | 8G | 9G | 9G | 9G | 9G | 9G | 5G | 8G | 0 | 0 |
| MORNING GLORY | 8H | 9G | 8H | 9G | 3C,8H | 9G | 5G | 7H | 0 | 0 |
| COCKLEBUR | 8H | 8H | 3C,5H | 8H | 3C,5H | 9H | 2C,2G | 3C,6H | 0 | 0 |
| NUTSEDGE | 3G | 10E | 7G | 10E | 5G | 9G | 0 | 2C,6G | 0 | 0 |
| CRABGRASS | 6G | 8G | 0 | 0 | 0 | 3G | 0 | 5G | 0 | 0 |
| BARNYARD GRASS | 7G | 8H | 3G | 3C,8H | 3C,6H | 9H | 2C | 9H | 0 | 0 |
| WILD OATS | 1C | 3G | 0 | 0 | 2G | 4G | 0 | 2C,5G | 0 | 0 |
| WHEAT | 2G | 5G | 0 | 2G | 0 | 6G | 0 | 2G | 0 | 0 |
| CORN | 3G | 3C,7H | 0 | 3C,8G | 0 | 2C,5G | 2C,3G | 3C,8G | 0 | 0 |
| SOYBEAN | 1C,2H | 3C,6H | 4H | 9H | 1C | 3C,6H | 3G | 3C,7H | 0 | 0 |
| RICE | 7G | 3C,9H | 7G | 8H | 4G | 9H | 3G | 3C,7G | 0 | 0 |
| SORGHUM | 6G | 9H | 2C,4G | 9H | 3G | 9H | 3C,5G | 3C,8H | 0 | 0 |
| CHEATGRASS | 6G | 6G | 2G | 5G | 5G | 6G | 0 | 7G | 0 | 0 |
| SUGAR BEETS | 8H | 3C,8G | 8G | 4C,9G | 8G | 3C,9G | 7G | 8G | 0 | 0 |
| VELVETLEAF | 6G | 7G | 8G | 9G | 4G | 9G | 2H | 8G | 0 | 0 |
| GIANT FOXTAIL | 2G | 6G | 0 | 4G | 0 | 4G | 0 | 3C,8G | 0 | 0 |
| BARLEY | 2C,6G | 3C,8G | 0 | 5G | 4G | 3C,7G | 0 | 2C,2G | 0 | 0 |

| | CMPD 11 | | CMPD 12 | | CMPD 13 | | CMPD 14 | |
|---|---|---|---|---|---|---|---|---|
| RATE = KG/HA | 0.01 | 0.05 | 0.05 | 0.4 | 0.01 | 0.05 | 0.05 | 0.4 |

POSTEMERGENCE

| | | | | | | | | |
|---|---|---|---|---|---|---|---|---|
| COTTON | 2C,8G | 4C,9G | 2C,8G | 10C | 4C,9G | 5C,9G | 10C | 9C |
| MORNING GLORY | 3C,8G | 9C | 2C,2G | 3C,3G | 10C | 10C | 10C | 10C |
| COCKLEBUR | 6G | 3C,8H | 2C,2G | 3C,7G | 3C,8H | 9C | 3C,9G | 4C,9G |
| NUTSEDGE | 7G | 3C,9G | 0 | 3C,7G | 5C,9G | 9C | 9G | 4C,9G |
| CRABGRASS | 0 | 4G | 0 | 3C,7G | 0 | 0 | 0 | 0 |
| BARNYARD GRASS | 0 | 0 | 0 | 4C,9M | 0 | 3C,4G | 2G | 2C,4G |
| WILD OATS | 0 | 0 | 0 | 2C | 0 | 0 | 0 | 0 |
| WHEAT | 0 | 0 | 0 | 7G | 0 | 0 | 0 | 0 |
| CORN | 0 | 0 | 0 | 8H | 0 | 2C,2H | 2G | 3G |
| SOYBEAN | 0 | 0 | 1H | 3C,4H | 5G | 2C,7G | 1H | 2C,3H |
| RICE | 0 | 0 | 0 | 2C,5G | 0 | 3G | 0 | 3G |
| SORGHUM | 0 | 0 | 0 | 2G | 2G | 2C,7H | 0 | 3C,6G |
| CHEATGRASS | 0 | 2G | 0 | 3C,6G | 0 | 4G | 0 | 3G |
| SUGAR BEETS | 0 | 1C,4G | 3C,3G | 3C,8G | 4C,8G | 5C,9G | 5G | 9G |

TABLE A-continued

| | | | | | | | | |
|---|---|---|---|---|---|---|---|---|
| VELVETLEAF | 4C,9G | 10C | 4H | 3C,8H | 10C | 10C | 9C | 10C |
| GIANT FOXTAIL | 0 | 3G | 3G | 3C,8G | 0 | 3C,4G | 0 | 2C,3G |
| BARLEY | 0 | 0 | 0 | 1C | 0 | 1C | 0 | — |
| PREEMERGENCE | | | | | | | | |
| COTTON | 4G | 5G | 3C,8H | 3C,9G | 2G | 8G | 7G | 9G |
| MORNING GLORY | 1C,2G | 2C,8G | 7H | 9G | 3C,7H | 8H | 8G | 9G |
| COCKLEBUR | 0 | 2C,5H | 1C | 3C,5H | 3C,5G | 7H | 5H | 9H |
| NUTSEDGE | 0 | 0 | 2C | 9G | 4G | 10E | 9G | 10E |
| CRABGRASS | 0 | 0 | 3C,5G | 9H | 0 | 0 | 0 | 3G |
| BARNYARD GRASS | 0 | 0 | 3C,9H | 9H | 2G | 8H | 1H | 3C,8G |
| WILD OATS | 0 | 0 | 0 | 3C,9H | 0 | 4G | 0 | 0 |
| WHEAT | 0 | 0 | 0 | 3C,8H | 0 | 0 | 0 | 0 |
| CORN | 0 | 0 | 3C,5G | 3C,8H | 2G | 2C,5G | 0 | 1H |
| SOYBEAN | 0 | 1C,2G | 3C,2H | 3C,7H | 3C,4H | 7G | 1H | 3H |
| RICE | 0 | 2G | 1C | 4C,9H | 0 | 7G | 0 | 6G |
| SORGHUM | 0 | 2G | 1C | 3C,9H | 2G | 2C,8G | 1C | 3G |
| CHEATGRASS | 0 | 0 | 3C,6G | 2C,9G | 2G | 7G | 0 | 0 |
| SUGAR BEETS | 3G | 7G | 4C,8G | 3C,9G | 8G | 9G | 8G | 9G |
| VELVETLEAF | 2G | 9G | 7H | 3C,9G | 8H | 9G | 7G | 9G |
| GIANT FOXTAIL | 0 | 3G | 3C,8H | 3C,9H | 2G | 4G | 0 | 3G |
| BARLEY | 0 | 0 | 0 | 3C,8G | 0 | 4G | 0 | 0 |

Test B

Test Description

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanquinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*), and teaweed (Sida spinosa). The second pot was planted with green foxtail (*Setaria viridis*), cocklebur (*Xantium pensylvanicum*), morningglory (*Ipomoea hederacea*), cotton (*Gossypium hirsutum*), johnsongrass (*Sorghum halepense*), barnyardgrass (*Echinochloa crusgalli*), corn (*Zea mays*), soybean (*Glycine max*) and giant foxtail (*Setaria faberii*). The third pot was planted with wheat (*Triticum aestivum*), barley (*Hordeum vulgare*), wild buckwheat (*Polygonum convolvulus* L.), cheatgrass (*Bromus secalinus* L.), sugarbeet (*Beta vulgaris*), wild oat (*Avena fatua* L.), viola (*Viola arvensis*), blackgrass (*Alopecurus myosuroides*), and rape (*Brassica napus*). The plants were grown for approximately fourteen days, then sprayed postemergence with the chemicals dissolved in a nonphytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice, and teaweed. The second pot was planted with green foxtail, cocklebur, morningglory, cotton, johnsongrass, barnyardgrass, corn, soybean, and giant foxtail. The third pot was planted with wheat, barley, wild buckwheat, cheatgrass, sugarbeet, wild oat, viola, blackgrass and rape. The three pans were sprayed preemergence with the chemicals dissolved in a nonphytotoxic solvent.

Treated plants and controls were maintained in the greenhouse for approximately 24 days, then all rated plants were compared to controls and visually rated for plant response.

Response ratings are based on a scale of 0 to 100 where 0=no effect, and 100=complete control. A blank entry means no test.

Response ratings are contained in Table B.

TABLE B

| RATE = G/HA | CMPD 1 | | | | CMPD 2 | | | | CMPD 3 | | | | CMPD 5 | | | | CMPD 6 | | | | |
|---|---|---|---|---|---|---|---|---|---|---|---|---|---|---|---|---|---|---|---|---|---|
| | 0016 | 0062 | 0250 | 1000 | 0004 | 0016 | 0062 | 0250 | 1000 | 0016 | 0062 | 0250 | 1000 | 0016 | 0062 | 0250 | 1000 | 0004 | 0016 | 0062 | 0250 | 1000 |
| POSTEMERGENCE | | | | | | | | | | | | | | | | | | | | | | |
| GIANT FOXTAIL | 0 | 0 | 20 | 40 | 0 | 0 | 70 | 90 | 90 | 0 | 0 | 0 | 40 | 0 | 0 | 0 | 100 | | 0 | 30 | 50 | |
| VELVETLEAF | 0 | 0 | 30 | 70 | 90 | 100 | 100 | 100 | 100 | 60 | 80 | 100 | 100 | 30 | 100 | 100 | 100 | | 40 | 60 | 100 | |
| SUGAR BEETS | 0 | 30 | 50 | 70 | 70 | 70 | 100 | 100 | 100 | 20 | 50 | 100 | 90 | 90 | 100 | 100 | 100 | | 70 | 80 | 90 | |
| CRABGRASS | 0 | 0 | 30 | 50 | 0 | 20 | 30 | 40 | 50 | 20 | 30 | 60 | 70 | 70 | 30 | 40 | 30 | | 0 | 0 | 0 | |
| TEAWEED | 0 | 0 | 0 | 50 | 60 | 90 | 100 | 100 | 100 | 0 | 20 | 50 | 70 | 0 | 70 | 80 | 100 | | 30 | 50 | 80 | |
| JIMSONWEED | 0 | 0 | 30 | 50 | 50 | 90 | 100 | 100 | 100 | 0 | 60 | 70 | 70 | 0 | 80 | 90 | 100 | | 50 | 90 | 100 | |
| RICE | 0 | 0 | 0 | 20 | 0 | 20 | 40 | 70 | 70 | 0 | 20 | 50 | 40 | 0 | 30 | 50 | 90 | | 30 | 50 | 70 | |
| COCKLEBUR | 30 | 30 | 50 | 70 | 50 | 80 | 100 | 100 | 100 | 30 | 80 | 80 | 90 | 0 | 90 | 100 | 100 | | 70 | 90 | 100 | |
| COTTON | 30 | 0 | 40 | 50 | 0 | 20 | 70 | 100 | 100 | 0 | 50 | 80 | 100 | 0 | 100 | 100 | 100 | | 50 | 60 | 100 | |
| SOYBEAN | 0 | 0 | 0 | 60 | 0 | 0 | 60 | 80 | 80 | 0 | 20 | 50 | 70 | 0 | 40 | 40 | 80 | | 50 | 30 | 70 | |
| BARNYARD GRASS | 0 | 0 | 30 | 30 | 0 | 0 | 90 | 70 | 90 | 0 | 0 | 0 | 30 | 0 | 0 | 0 | 50 | | 50 | 30 | 70 | |
| WILD OATS | 0 | 0 | 0 | 30 | 0 | 0 | 0 | 0 | 0 | 0 | 0 | 0 | 0 | 0 | 0 | 0 | 20 | | 0 | 30 | 0 | |
| MORNINGGLORY | 0 | 0 | 30 | 50 | 50 | 80 | 100 | 100 | 100 | 0 | 40 | 80 | 90 | 0 | 100 | 100 | 100 | | 30 | 60 | 100 | |
| WHEAT | 0 | 0 | 0 | 30 | 0 | 0 | 0 | 0 | 20 | 0 | 0 | 0 | 0 | 0 | 0 | 0 | 0 | | 0 | 0 | 0 | |
| CASSIA | 0 | 0 | 20 | 40 | 0 | 0 | 20 | 20 | 40 | 0 | 0 | 50 | 60 | 0 | 0 | 60 | 100 | | 0 | 0 | 30 | |
| JOHNSONGRASS | 0 | 0 | 20 | 30 | 0 | 20 | 50 | 80 | 60 | 0 | 0 | 20 | 70 | 0 | 30 | 50 | 90 | | 30 | 50 | 70 | |
| NUTSEDGE | 0 | 0 | 30 | 100 | 0 | 70 | 90 | 90 | 100 | 0 | 60 | 80 | 70 | 0 | 100 | 100 | 100 | | 70 | 90 | 100 | |
| CORN | 0 | 0 | 0 | 0 | 0 | 0 | 100 | 50 | 20 | 0 | 0 | 0 | 20 | 0 | 0 | 20 | 30 | | 0 | 0 | 0 | |
| WILD BUCKWHEAT | 0 | 30 | 60 | 100 | 90 | 100 | 100 | 100 | 100 | 80 | 100 | 100 | 100 | 30 | 100 | 100 | 100 | | 90 | 100 | 100 | |
| BLACK GRASS | 0 | 30 | 50 | 70 | 0 | 20 | 50 | 60 | 60 | 0 | 0 | 20 | 50 | 60 | 0 | 30 | 90 | | 0 | 0 | 30 | |
| RAPESEED | 0 | 30 | 70 | 100 | 70 | 90 | 100 | 100 | 100 | 90 | 100 | 80 | 100 | 100 | 100 | 100 | 100 | | 100 | 100 | 100 | |
| BARLEY | 0 | 0 | 0 | 20 | 0 | 20 | 20 | 30 | 20 | 0 | 0 | 20 | 20 | 0 | 0 | 20 | 30 | | 0 | 30 | 50 | |
| GREEN FOXTAIL | 0 | 0 | 30 | 60 | 0 | 50 | 60 | 100 | 40 | 0 | 0 | 80 | 40 | 0 | 0 | 30 | 90 | | 0 | 30 | 50 | |
| CHEAT GRASS | 0 | 0 | 30 | 70 | 0 | 20 | 90 | 90 | 90 | 20 | 50 | 80 | 80 | 0 | 50 | 30 | 100 | | 50 | 30 | 60 | |
| VIOLA | 0 | 30 | 50 | 70 | 40 | 60 | 90 | 100 | 80 | 40 | 50 | 80 | 70 | 0 | 70 | 90 | 90 | | 50 | 70 | 90 | |
| LAMBSQUARTER | 20 | 30 | 50 | 70 | 50 | 80 | 100 | 100 | 100 | 80 | 100 | 100 | 70 | 0 | 60 | 90 | 90 | | 50 | 70 | 90 | |
| PREEMERGENCE | | | | | | | | | | | | | | | | | | | | | | |
| GIANT FOXTAIL | 30 | 50 | 70 | 90 | 30 | 50 | 70 | 100 | 100 | 30 | 30 | 40 | 90 | 60 | 70 | 100 | 100 | 0 | 30 | 50 | 70 | 100 |
| VELVETLEAF | 0 | 30 | 50 | 70 | 50 | 60 | 100 | 100 | 100 | 100 | 100 | 100 | 90 | 70 | 90 | 90 | 100 | 40 | 30 | 50 | 70 | 90 |
| SUGAR BEETS | 50 | 70 | 80 | 90 | 90 | 90 | 100 | 100 | 100 | 60 | 60 | 90 | 90 | 80 | 90 | 100 | 100 | 40 | 60 | 70 | 80 | 70 |
| CRABGRASS | 0 | 0 | 30 | 50 | 30 | 0 | 0 | 50 | 60 | 0 | 20 | 30 | 40 | 0 | 0 | 0 | 30 | 0 | 0 | 30 | 40 | 90 |
| TEAWEED | 0 | 30 | 50 | 90 | 30 | 50 | 100 | 100 | 100 | 40 | 80 | 80 | 90 | 50 | 70 | 80 | 100 | 0 | 30 | 60 | 80 | 90 |
| JIMSONWEED | 30 | 50 | 70 | 90 | 40 | 60 | 100 | 100 | 100 | 50 | 30 | 60 | 80 | 30 | 70 | 90 | 100 | 0 | 50 | 90 | 80 | 90 |
| RICE | 0 | 0 | 30 | 30 | 0 | 0 | 40 | 80 | 30 | 30 | 50 | 50 | 30 | 30 | 40 | 50 | 100 | 20 | 30 | 50 | 100 | 100 |
| COCKLEBUR | 0 | 30 | 50 | 70 | 30 | 80 | 90 | 100 | 100 | 70 | 80 | 80 | 100 | 50 | 70 | 80 | 90 | 20 | 60 | 70 | 80 | 90 |
| COTTON | 0 | 30 | 40 | 70 | 30 | 20 | 70 | 90 | 100 | 20 | 80 | 90 | 100 | 70 | 50 | 60 | 80 | 40 | 40 | 60 | 60 | 70 |
| SOYBEAN | 0 | 0 | 30 | 30 | 20 | 50 | 60 | 100 | 60 | 20 | 20 | 70 | 60 | 0 | 30 | 30 | 50 | 20 | 0 | 30 | 30 | 100 |
| BARNYARD GRASS | 30 | 50 | 70 | 70 | 30 | 50 | 90 | 100 | 100 | 20 | 20 | 30 | 100 | 30 | 50 | 70 | 90 | 40 | 50 | 50 | 50 | 90 |
| WILD OATS | 0 | 0 | 30 | 90 | 30 | 0 | 60 | 70 | 50 | 0 | 0 | 30 | 60 | 0 | 30 | 0 | 20 | 20 | 0 | 30 | 30 | 50 |
| MORNINGGLORY | 30 | 50 | 70 | 90 | 20 | 60 | 90 | 100 | 100 | 40 | 60 | 80 | 100 | 50 | 70 | 80 | 90 | 40 | 50 | 60 | 70 | 90 |
| WHEAT | 0 | 0 | 30 | 30 | 0 | 0 | 40 | 20 | 40 | 0 | 0 | 30 | 20 | 0 | 50 | 0 | 100 | 0 | 0 | 30 | 0 | 30 |
| CASSIA | 0 | 40 | 50 | 50 | 0 | 40 | 60 | 80 | 80 | 30 | 0 | 20 | 100 | 70 | 50 | 70 | 100 | 30 | 30 | 30 | 50 | 70 |
| JOHNSONGRASS | 30 | 0 | 30 | 50 | 40 | 60 | 90 | 90 | 100 | 30 | 40 | 50 | 90 | 60 | 70 | 90 | 100 | 20 | 0 | 30 | 50 | 80 |
| NUTSEDGE | 0 | 30 | 50 | 30 | 30 | 50 | 100 | 90 | 100 | 50 | 60 | 80 | 30 | 40 | 60 | 100 | 100 | 40 | 60 | 60 | 90 | 100 |
| CORN | 0 | 0 | 0 | 0 | 40 | 0 | 0 | 0 | 20 | 50 | 0 | 0 | 100 | 90 | 90 | 30 | 80 | 0 | 0 | 30 | 30 | 70 |
| WILD BUCKWHEAT | 90 | 100 | 100 | 100 | 80 | 90 | 90 | 80 | 100 | 100 | 100 | 100 | 100 | 30 | 100 | 100 | 70 | 0 | 50 | 70 | 50 | 100 |
| BLACK GRASS | 0 | 50 | 70 | 30 | 20 | 50 | 50 | 80 | 80 | 40 | 40 | 80 | 100 | 100 | 100 | 90 | 100 | 30 | 0 | 30 | 100 | 100 |
| RAPESEED | 0 | 0 | 0 | 30 | 70 | 90 | 80 | 90 | 70 | 40 | 80 | 100 | 100 | 50 | 80 | 100 | 70 | 100 | 100 | 100 | 100 | 50 |

TABLE B-continued

| | | | | | | | | | | | | | | | | | | | | | | | | |
|---|---|---|---|---|---|---|---|---|---|---|---|---|---|---|---|---|---|---|---|---|---|---|---|---|
| GREEN FOXTAIL | 30 | 50 | 70 | 90 | 30 | 70 | 100 | 100 | | | 100 | 100 | 70 | 100 | 100 | | | 90 | 30 | 50 | 70 | 100 |
| CHEAT GRASS | 0 | 30 | 60 | 80 | 20 | 50 | 60 | 90 | | | 100 | 90 | 50 | 30 | 50 | | | 100 | 0 | 30 | 50 | 70 |
| VIOLA | 70 | 80 | 90 | 100 | 80 | 90 | 100 | 100 | | | 100 | 100 | 90 | 80 | 90 | | | 100 | 80 | 90 | 100 | 100 |
| LAMBSQUARTER | 50 | 70 | 100 | 100 | 60 | 90 | 100 | 100 | | | 100 | 100 | 100 | 70 | 100 | | | 100 | 70 | 90 | 100 | 100 |

| | CMPD 7 | | | | CMPD 8 | | | | | | | | CMPD 11 | | | | CMPD 12 | | | | CMPD 13 | | | CMPD 14 | | | |
|---|---|---|---|---|---|---|---|---|---|---|---|---|---|---|---|---|---|---|---|---|---|---|---|---|---|---|---|---|
| RATE = G/HA | 0016 | 0062 | 0250 | 1000 | 0016 | 0062 | 0250 | 1000 | 0004 | 0016 | 0062 | 0250 | 0004 | 0016 | 0062 | 0250 | 0062 | 0250 | 0500 | 1000 | 0004 | 0016 | 0062 | 0004 | 0016 | 0062 | 0250 |
| POSTEMERGENCE | | | | | | | | | | | | | | | | | | | | | | | | | | | |
| GIANT FOXTAIL | 0 | 30 | 50 | 60 | 30 | 50 | 70 | | 100 | 100 | 0 | 0 | 0 | 0 | 0 | 0 | 30 | 50 | 50 | 90 | 0 | 0 | 40 | 0 | 0 | 20 | 30 |
| VELVETLEAF | 50 | 70 | 100 | 90 | 40 | 70 | 80 | | 100 | 100 | 100 | 80 | 20 | 30 | 30 | 0 | 50 | 70 | 90 | 70 | 100 | 100 | 100 | 0 | 70 | 80 | 90 |
| SUGAR BEETS | 70 | 90 | 100 | 70 | 80 | 90 | 100 | | 50 | 70 | 100 | 90 | 0 | 0 | 50 | 30 | 60 | 80 | 70 | 50 | 90 | 100 | 100 | 0 | 50 | 90 | 90 |
| CRABGRASS | 0 | 0 | 30 | 100 | 30 | 50 | 70 | 90 | 0 | 0 | 30 | 60 | 0 | 0 | 30 | 30 | 50 | 80 | 80 | 100 | 30 | 70 | 80 | 0 | 0 | 0 | 0 |
| TEAWEED | 70 | 70 | 100 | 90 | 40 | 70 | 90 | 100 | 50 | 70 | 70 | 90 | 0 | 0 | 0 | 30 | 30 | 70 | 70 | 90 | 50 | 90 | 90 | 0 | 70 | 80 | 70 |
| JIMSONWEED | 80 | 80 | 100 | 100 | 70 | 80 | 100 | 100 | 0 | 50 | 50 | 70 | 0 | 20 | 0 | 0 | 30 | 60 | 60 | 80 | 70 | 100 | 100 | 20 | 20 | 60 | 70 |
| RICE | 50 | 50 | 70 | 90 | 50 | 50 | 70 | 80 | 0 | 0 | 0 | 0 | 0 | 0 | 40 | 0 | 30 | 30 | 50 | 80 | 30 | 30 | 30 | 30 | 20 | 20 | 40 |
| COCKLEBUR | 30 | 80 | 100 | 80 | 30 | 80 | 100 | 100 | 30 | 90 | 60 | 80 | 0 | 0 | 0 | 0 | 30 | 60 | 70 | 90 | 50 | 60 | 80 | 20 | 30 | 70 | 80 |
| COTTON | 70 | 70 | 100 | 100 | 70 | 50 | 100 | 90 | 90 | 0 | 100 | 60 | 20 | 0 | 40 | 0 | 30 | 60 | 80 | 90 | 30 | 40 | 100 | 30 | 20 | 70 | 70 |
| SOYBEAN | 50 | 60 | 80 | 90 | 70 | 90 | 100 | 90 | 0 | 0 | 40 | 0 | 0 | 20 | 20 | 0 | 60 | 70 | 70 | 80 | 40 | 0 | 50 | 0 | 30 | 70 | 70 |
| BARNYARD GRASS | 30 | 60 | 80 | 0 | 0 | 30 | 60 | 90 | 30 | 90 | 30 | 20 | 0 | 0 | 20 | 30 | 30 | 60 | 40 | 30 | 30 | 0 | 40 | 30 | 20 | 30 | 80 |
| WILD OATS | 0 | 30 | 0 | 80 | 30 | 50 | 0 | 50 | 0 | 0 | 0 | 50 | 0 | 0 | 50 | 0 | 0 | 0 | 0 | 0 | 0 | 40 | 0 | 0 | 0 | 70 | 30 |
| MORNINGGLORY | 40 | 60 | 80 | 0 | 40 | 60 | 80 | 100 | 50 | 0 | 0 | 0 | 30 | 40 | 0 | 0 | 30 | 30 | 70 | 70 | 50 | 0 | 100 | 30 | 20 | 70 | 70 |
| WHEAT | 0 | 0 | 0 | 90 | 0 | 0 | 0 | 60 | 0 | 0 | 0 | 30 | 0 | 0 | 0 | 30 | 0 | 0 | 0 | 20 | 0 | 0 | 0 | 0 | 0 | 0 | 0 |
| CASSIA | 30 | 50 | 50 | 80 | 30 | 50 | 70 | 100 | 50 | 0 | 50 | 0 | 0 | 0 | 50 | 0 | 20 | 50 | 50 | 90 | 40 | 40 | 50 | 0 | 0 | 0 | 90 |
| JOHNSONGRASS | 50 | 70 | 70 | 100 | 20 | 40 | 60 | 100 | 0 | 0 | 100 | 0 | 0 | 0 | 0 | 0 | 70 | 60 | 80 | 80 | 50 | 50 | 70 | 0 | 70 | 80 | 0 |
| NUTSEDGE | 0 | 0 | 0 | 0 | 70 | 100 | 100 | 100 | 50 | 100 | 100 | 30 | 30 | 0 | 0 | 0 | 0 | 80 | 60 | 80 | 60 | 0 | 100 | 0 | 0 | 0 | 70 |
| CORN | 0 | 0 | 0 | | 0 | 0 | 0 | | 30 | 0 | 0 | 0 | 0 | 0 | 0 | 0 | 0 | 30 | 30 | 0 | 20 | 30 | 20 | 0 | 0 | 80 | 0 |
| WILD BUCKWHEAT | 90 | 100 | 100 | | 50 | 70 | 90 | | 30 | 70 | 70 | 80 | 30 | 0 | 50 | 0 | 70 | 80 | 80 | 70 | 70 | 80 | 90 | 0 | 20 | 80 | 20 |
| BLACK GRASS | 0 | 0 | 30 | | 30 | 50 | 70 | | 70 | 0 | 100 | 0 | 20 | 0 | 0 | 30 | 0 | 0 | 0 | 0 | 0 | 0 | 0 | 70 | 70 | 0 | 90 |
| RAPESEED | 90 | 100 | 100 | | 100 | 100 | 100 | | 0 | 0 | 40 | 50 | 0 | 0 | 30 | 0 | 100 | 0 | 0 | 0 | 100 | 0 | 100 | 0 | 0 | 0 | 0 |
| BARLEY | 0 | 0 | 0 | | 20 | 40 | 40 | | 0 | 0 | 0 | 30 | 0 | 0 | 40 | 30 | 0 | 30 | 60 | 0 | 0 | 30 | 50 | 0 | 0 | 0 | 0 |
| GREEN FOXTAIL | 30 | 50 | 50 | | 80 | 90 | 100 | | 0 | 0 | 30 | 70 | 0 | 0 | 30 | 0 | 40 | 60 | 60 | 90 | 40 | 40 | 60 | 70 | 20 | 0 | 20 |
| CHEAT GRASS | 50 | 70 | 70 | | 50 | 70 | 100 | | 0 | 0 | 0 | 0 | 30 | 30 | 50 | 0 | 30 | 50 | 60 | 90 | 0 | 70 | 90 | 0 | 70 | 30 | 90 |
| VIOLA | 0 | 0 | 90 | | 80 | 90 | 100 | | 30 | 30 | 50 | 30 | 0 | 0 | 0 | 0 | 40 | 70 | 80 | 0 | 40 | 40 | 0 | 50 | 0 | 0 | 0 |
| LAMBSQUARTER | 50 | 70 | 90 | | 50 | 70 | 90 | | 0 | 0 | 30 | 0 | 0 | 0 | 0 | 0 | 50 | 70 | 60 | 0 | 70 | 70 | 90 | 20 | 30 | 90 | 90 |
| PREEMERGENCE | | | | | | | | | | | | | | | | | | | | | | | | | | | |
| GIANT FOXTAIL | 0 | 0 | 30 | 60 | 30 | 50 | 70 | 90 | 0 | 0 | 30 | 0 | 0 | 0 | 30 | 0 | 50 | 70 | 70 | 70 | 30 | 50 | 70 | 0 | 0 | 0 | 30 |
| VELVETLEAF | 40 | 70 | 80 | 90 | 40 | 80 | 80 | 90 | 100 | 100 | 60 | 80 | 50 | 30 | 50 | 0 | 60 | 80 | 80 | 80 | 90 | 90 | 100 | 90 | 100 | 100 | 100 |
| SUGAR BEETS | 50 | 70 | 80 | 70 | 50 | 80 | 90 | 90 | 50 | 0 | 70 | 90 | 0 | 50 | 70 | 0 | 60 | 90 | 90 | 80 | 90 | 80 | 100 | 70 | 70 | 80 | 100 |
| CRABGRASS | 0 | 0 | 30 | 70 | 0 | 0 | 30 | 60 | 0 | 0 | 30 | 60 | 0 | 0 | 30 | 0 | 50 | 30 | 50 | 100 | 30 | 30 | 50 | 0 | 0 | 30 | 30 |
| TEAWEED | 50 | 80 | 80 | 90 | 70 | 80 | 90 | 100 | 0 | 0 | 70 | 90 | 0 | 0 | 50 | 0 | 50 | 70 | 70 | 80 | 50 | 80 | 90 | 0 | 60 | 60 | 70 |
| JIMSONWEED | 70 | 80 | 80 | 90 | 80 | 80 | 90 | 100 | 50 | 50 | 50 | 70 | 0 | 0 | 30 | 0 | 70 | 70 | 70 | 90 | 60 | 60 | 70 | 20 | 0 | 30 | 40 |
| RICE | 50 | 70 | 70 | 80 | 30 | 50 | 80 | 80 | 0 | 30 | 60 | 50 | 0 | 0 | 30 | 0 | 50 | 80 | 80 | 90 | 50 | 50 | 90 | 30 | 30 | 80 | 80 |
| COCKLEBUR | 30 | 70 | 80 | 70 | 50 | 60 | 80 | 90 | 0 | 90 | 70 | 80 | 20 | 0 | 50 | 20 | 70 | 70 | 80 | 80 | 60 | 80 | 70 | 40 | 60 | 70 | 80 |
| COTTON | 50 | 80 | 80 | 80 | 50 | 70 | 80 | 80 | 0 | 0 | 60 | 60 | 0 | 0 | 30 | 0 | 60 | 30 | 30 | 30 | 0 | 0 | 30 | 50 | 70 | 80 | 70 |
| SOYBEAN | 60 | 80 | 80 | 100 | 60 | 70 | 80 | 80 | 0 | 0 | 40 | 20 | 0 | 0 | 40 | 0 | 50 | 50 | 30 | 50 | 30 | 50 | 50 | 0 | 0 | 40 | 20 |
| BARNYARD GRASS | 30 | 50 | 70 | 50 | 30 | 30 | 60 | 50 | 0 | 30 | 40 | 30 | 0 | 30 | 30 | 80 | 50 | 70 | 70 | 80 | 50 | 30 | 80 | 40 | 50 | 40 | 70 |
| WILD OATS | 30 | 50 | 50 | 0 | 0 | 30 | 30 | 70 | 0 | 0 | 40 | 70 | 0 | 0 | 0 | 30 | 50 | 30 | 30 | 20 | 0 | 0 | 0 | 0 | 40 | 0 | 20 |
| MORNINGGLORY | 50 | 70 | 80 | 90 | 30 | 60 | 70 | 0 | 0 | 0 | 0 | 30 | 0 | 0 | 0 | 0 | 70 | 70 | 70 | 90 | 40 | 0 | 80 | 60 | 60 | 90 | 90 |
| WHEAT | 0 | 0 | 0 | 90 | 0 | 0 | 30 | 40 | 0 | 0 | 50 | 0 | 0 | 0 | 0 | 30 | 40 | 0 | 30 | 30 | 0 | 30 | 0 | 20 | 20 | 30 | 10 |
| CASSIA | 0 | 30 | 60 | 100 | 0 | 20 | 30 | 90 | 0 | 30 | 30 | 50 | 0 | 30 | 30 | 0 | 50 | 50 | 50 | 50 | 50 | 60 | 70 | 0 | 30 | 40 | 100 |
| JOHNSONGRASS | 0 | 30 | 60 | 80 | 20 | 0 | 50 | 70 | 0 | 0 | 0 | 30 | 0 | 0 | 40 | 0 | 20 | 70 | 60 | 70 | 30 | 30 | 40 | 50 | 0 | 0 | 20 |
| NUTSEDGE | 50 | 70 | 90 | 100 | 80 | 30 | 100 | 100 | 0 | 0 | 0 | 50 | 0 | 0 | 0 | 30 | 30 | 30 | 30 | 40 | 50 | 40 | 100 | 50 | 80 | 90 | 100 |
| CORN | 0 | 0 | 20 | 40 | 50 | 20 | 30 | 50 | 0 | 0 | 0 | 0 | 0 | 0 | 0 | 0 | 20 | 30 | 30 | 40 | 0 | 0 | 0 | 0 | 0 | 0 | 10 |

TABLE B-continued

| | | | | | | | | | | | | | | | | | | | | | | | |
|---|---|---|---|---|---|---|---|---|---|---|---|---|---|---|---|---|---|---|---|---|---|---|---|
| WILD BUCKWHEAT | 50 | 70 | 90 | 100 | 70 | 80 | 90 | 100 | 60 | 80 | 30 | 50 | 60 | 70 | 80 | 90 | 40 | 60 | 80 | 0 | 0 | 40 | 50 |
| BLACK GRASS | 0 | 30 | 50 | 70 | 0 | 30 | 50 | 70 | 60 | 100 | 0 | 20 | 0 | 30 | 50 | 70 | 0 | 0 | 0 | 0 | 30 | 30 | 100 |
| RAPESEED | 70 | 90 | 100 | 100 | 90 | 100 | 100 | 100 | 60 | 70 | 0 | 0 | 30 | 50 | 70 | 90 | 80 | 90 | 100 | 80 | 100 | 100 | 100 |
| BARLEY | 0 | 0 | 20 | 30 | 0 | 20 | 40 | 70 | 0 | 0 | 0 | 0 | 0 | 0 | 0 | 0 | 0 | 0 | 0 | 0 | 0 | 0 | 0 |
| GREEN FOXTAIL | 0 | 0 | 30 | 60 | 40 | 60 | 80 | 90 | 0 | 0 | 0 | 30 | 60 | 100 | 100 | 100 | 30 | 50 | 70 | 0 | 0 | 0 | 40 |
| CHEAT GRASS | 0 | 30 | 80 | 100 | 0 | 30 | 50 | 70 | 0 | 0 | 0 | 0 | 0 | 30 | 50 | 60 | 0 | 30 | 50 | 70 | 80 | 20 | 90 |
| VIOLA | 60 | 80 | 100 | 100 | 50 | 70 | 80 | 90 | 70 | 100 | 0 | 0 | 0 | 0 | 0 | 0 | 0 | 0 | 0 | 30 | 80 | 70 | 80 |
| LAMBSQUARTER | 100 | 100 | 100 | 100 | 90 | 100 | 100 | 100 | 90 | 100 | 60 | 70 | 80 | 90 | 100 | 100 | 80 | 90 | 90 | 60 | | | |

ABBREVIATIONS
SBN = Soybeans
CRN = Corn
WHT = Wheat
BAR = Barley
WBW = Wild Buckwheat
CHT = Cheatgrass
SBT = Sugar beets
WIO = Wild Oats
VIO = Viola
BKG = Blackgrass
RAP = Rape
NUT = Nutsedge
CRB = Crabgrass
CAS = Cassia
TEA = Teaweed
JMW = Jimsonweed
VEL = Velvetleaf
LBQ = Lambsquarter
RCE = Rice
GRF = Green Foxtail
CKL = Cocklebur
MOG = Morningglory
COT = Cotton
JNG = Johnsongrass
BYG = Barnyardgrass
GFX = Giant Foxtail

Test C

The purpose of this screen is to identify and characterize potential sugarbeet herbicides.

Seeds of the following crops and weeds are sown into 18 cm diameter plastic pots containing steamsterilized Sassafras sandy loam soil (0.8% organic soil, pH 6.7): spring wheat (*Triticum gestivum*), spring barley (*Hordeum vulgare*), sugarbeets (*Beta vulgaris*), black nightshade (*Solanum nigrum*), chickweed (*Stellaria media*), cleavers (*Galium aparine*), common lambsquarters (*Chenopodium album*), knotweed (*Polygonum aviculare*), kochia (*Kochia scoparia*), matricaria (*Matricaria indora*), redroot pigweed (*Amaranthus retroflexus*), speedwell (*Veronica persica*), wild mustard (*Sinapis arvensis*), wild radish (*Raphinus raphinistrum*), smartweed (*Polygonum pericaria*), black bindweed (*Polygonum convolvulus*), annular bluegrass (*Poa annua*), annual ryegrass (*Lolium multiflorum*), blackgrass (*Alopecurus myosuroides*), green foxtail (*Setaria viridis*), and wild oats (*Avena fatua*).

The compound tested is formulated in a nonphytotoxic solvent and applied as a spray to the soil (preemergence) or to the foliage and soil (postemergence). Plants are treated at three stages: (1) preemergence, (2) postemergence when the sugarbeets are in the 1-2 leaf stage (Post 1), and (3) postemergence when the sugarbeets are in the 3-4 leaf stage (Post 2). Plants are grown in a temperature-controlled greehouse for the duration of the experiment.

Weed control and crop injury are evaluated visually (38 days after the Pre treatment, 28 days after Post treatment 1, and 11 days after Post treatment 2). Ratings are expressed using a scale of 0 to 100, where 0 means no injury or control and 100 means complete death of the plants. The ratings are summarized in Table C.

TABLE C

| CMPD 11 | | | | |
|---|---|---|---|---|
| RATE GM/HA | 0030 | 0063 | 0125 | 0250 |
| PREEMERGENCE | | | | |
| WHEAT | 25 | 25 | 25 | 25 |
| BARLEY | 25 | 25 | 35 | 25 |
| SUGARBEET CROPS | 35 | 35 | 40 | 40 |
| BLCK NIGHTSHADE | 30 | 65 | 90 | 90 |
| CHICK WEED | 70 | 70 | 70 | 100 |
| LAMBSQUARTER | 70 | 90 | 70 | 100 |
| GALIUM | 50 | 90 | 100 | 100 |
| KNOT WEED | 20 | 100 | 95 | 100 |
| KOCHIA | 100 | 100 | 100 | 100 |
| MATRA INDORA | 25 | 50 | 90 | 100 |
| PIG WEED | 30 | 60 | 70 | 75 |
| SMART WEED | 100 | 70 | 50 | 50 |
| SPEEDWELL | 60 | 70 | 50 | 100 |
| BUCKWHEAT | 70 | 95 | 100 | 100 |
| MUSTARD | 100 | 100 | 100 | 100 |
| WILD RADISH | 90 | 95 | 95 | 95 |
| BLUE GRASS | 0 | 0 | 0 | 0 |
| RYE GRASS | 0 | 0 | 0 | 0 |
| BLACK GRASS | 0 | 20 | 50 | 20 |
| GREEN FOXTAIL | 0 | 0 | 0 | 0 |
| WILD OATS | 0 | 25 | 0 | 20 |
| RATE GM/HA | 0016 | 0030 | 0063 | 0125 |
| POSTEMERGENCE 1 | | | | |
| WHEAT | 0 | 0 | 0 | 0 |
| BARLEY | 0 | 0 | 0 | 10 |
| SUGARBEET CROPS | 0 | 10 | 20 | 25 |
| BLCK NIGHTSHADE | 80 | 90 | 90 | 100 |
| CHICK WEED | 40 | 50 | 60 | 90 |
| LAMBSQUARTER | 0 | 0 | 20 | 0 |
| GALIUM | 50 | 80 | 100 | 100 |
| KNOT WEED | 0 | 0 | 0 | 20 |
| KOCHIA | 0 | 100 | 100 | 100 |
| MATRA INDORA | 0 | 30 | 75 | 100 |
| PIG WEED | 40 | 60 | 75 | 75 |
| SMART WEED | 0 | 0 | 0 | 0 |
| SPEEDWELL | 50 | 50 | 20 | 20 |
| BUCKWHEAT | 0 | 50 | 90 | 100 |
| MUSTARD | 100 | 100 | 100 | 100 |
| WILD RADISH | 0 | 70 | 100 | 100 |
| BLUE GRASS | 0 | 0 | 20 | 20 |
| RYE GRASS | 0 | 0 | 0 | 0 |
| BLACK GRASS | 0 | 20 | 0 | 20 |
| GREEN FOXTAIL | 0 | 20 | 0 | 25 |
| WILD OATS | 0 | 0 | 20 | 0 |
| POSTEMERGENCE 2 | | | | |
| WHEAT | 10 | 20 | 20 | 0 |
| BARLEY | 20 | 20 | 20 | 10 |
| SUGARBEET CROPS | 15 | 40 | 40 | 40 |
| BLCK NIGHTSHADE | 60 | 50 | 50 | 50 |
| CHICK WEED | 80 | 80 | 90 | 90 |
| LAMBSQUARTER | 0 | 20 | 20 | 20 |
| GALIUM | 0 | 65 | 90 | 100 |
| KNOT WEED | 0 | 20 | 20 | 30 |
| KOCHIA | 100 | 100 | 100 | 100 |
| MATRA INDORA | 0 | 0 | 50 | 50 |
| PIG WEED | 80 | 70 | 70 | 70 |
| SMART WEED | 0 | 40 | 40 | 100 |
| SPEEDWELL | 60 | 50 | 50 | 30 |
| BUCKWHEAT | 0 | 25 | 25 | 90 |
| MUSTARD | 100 | 100 | 100 | 100 |
| WILD RADISH | 0 | 35 | 65 | 90 |
| BLUE GRASS | 10 | 0 | 25 | 0 |
| RYE GRASS | 0 | 20 | 0 | 0 |
| BLACK GRASS | 0 | 0 | 0 | 0 |
| GREEN FOXTAIL | 0 | 90 | 0 | 0 |
| WILD OATS | 20 | 0 | 0 | 0 |

Test D

The Corn and Sorghum Herbicide Test included the following species in both the preemergence and postemergence evaluations:

| Category | Common Name | Scientific Name |
|---|---|---|
| Crops | Corn | *Zea mays* |
| | Soybean | *Glycine max* |
| | Sorghum | *Sorghum bicolor* |
| Grasses | Green foxtail | *Setaria viridis* |
| | Giant foxtail | *Setaria faberii* |
| | Johnsongrass | *Sorghum halepense* |
| | Barnyardgrass | *Echinochloa crus-galli* |
| | Fall panicum | *Panicum dichotomiflorum* |
| | Crabgrass | *Digitaria sanguinalis* |
| | Nutsedge | *Cyperus rotundus* |
| Broadleaves | Cocklebur | *Xanthium pensylvanicum* |
| | Morningglory | *Ipomoea hederacea* |
| | Velvetleaf | *Abutilon theophrasti* |
| | Jimsonweed | *Datura stramonium* |
| | Lambsquarters | *Chenopodium album* |
| | Pigweed | *Amaranthus retroflexus* |
| | Smartweed | *Polygonum persicaris* |

POSTEMERGENCE

Postemergence plants were grown in Sassafras sandy loam soil (soil type A). Corn and soybeans were grown in separate 25 cm diameter containers. Sorghum and the seven grass weed species were grown in two 18 cm diameter containers, 4 species per container. The seven broadleaf weed species were also grown in two 18 cm diameter containers, 4 species in one container, 3 species in the second container. One additional planting of corn in an 18 cm diameter container was made. The soil surface of this additional container of corn was covered with the absorbent, perlite, before spray treatment so that test chemicals would enter the plant only via the foliage. The plants were grown 10–21 days, dependent upon the species and then sprayed postemergence with the test chemicals dissolved in a non-phytotoxic solvent.

PREEMERGENCE

Preemergence plantings were grown in fertilized Tama silt loam soil (soil type B). These plants were identical to those described in the postemergence section, with the exception of the corn planting having perlite covering the soil surface. These plantings were made the day of or the day before spraying the test chemicals dissolved in a non-phytotoxic solvent.

EVALUATION

Treated plants and controls were maintained in the greenhouse for 2 to 4 weeks. Visual planting response ratings were made on a percentage scale of 0 to 100 in comparison with a control where 0=no injury, and 100=death. The ratings are summarized in Table D.

pot. At the same time, seedlings of tubers of the following species were transplanted into the muddy soil: water plantain (*Alisma trivale*), Scirpus (*Scirpus mucranatus*), and Cyperus (*Cyperus difformis*). The weed species selected for this test are of economic importance in major rice-growing areas. The chemical treatments were applied directly to the paddy water after being formulated in a non-phytotoxic solvent within hours after transplanting of two additional species: water chestnut (Eleocharis spp.) and arrowhead (*Sagittaria latifolia*). Shortly after treatment, the drain hole was opened to drop the water level by two cm. Water was then added to restore the water level to its original height. The following day the draining and refilling process was repeated. The pots were then maintained in the greenhouse.

Rates of application and plant response ratings made 21 days after treatment are summarized in Table E. Response ratings are based on a scale of 0 to 100 where 0=no effect and 100=complete control.

TABLE D

| RATE GM/HA | CMPD 2 |      |      |      |      |      |      | CMPD 6 |      |      |      |      |      |
|---|---|---|---|---|---|---|---|---|---|---|---|---|---|
|  | 0002 | 0004 | 0008 | 0016 | 0031 | 0062 | 0125 | 0250 | 0008 | 0016 | 0031 | 0062 | 0125 | 0250 |
| PREEMERGENCE | | | | | | | | | | | | | | |
| SOIL TYPE |  |  | B | B | B | B | B | B | B | B | B | B | B | B |
| CORN |  |  | 0 | 0 | 0 | 15 | 25 | 45 |  | 0 | 0 | 0 | 20 | 35 |
| SOYBEAN |  |  | 0 | 10 | 20 | 40 | 55 | 65 |  | 0 | 0 | 20 | 35 | 55 |
| GREEN FXTL |  |  | 0 | 20 | 40 | 60 | 80 | 90 |  | 0 | 0 | 20 | 40 | 60 |
| GIANT FXTL |  |  | 0 | 20 | 30 | 50 | 75 | 95 |  | 0 | 0 | 0 | 35 | 45 |
| PANICUM |  |  | 0 | 20 | 40 | 56 | 85 | 100 |  | 0 | 0 | 25 | 45 | 65 |
| CRABGRASS |  |  | 0 | 0 | 0 | 0 | 20 | 40 |  | 0 | 0 | 0 | 0 | 20 |
| BARNYARDGRASS |  |  | 0 | 20 | 40 | 55 | 75 | 90 |  | 0 | 0 | 0 | 0 | 30 |
| JOHNSONGRASS |  |  | 55 | 65 | 75 | 85 | 95 | 100 |  | 0 | 0 | 30 | 65 | 80 |
| SORGHUM |  |  | 20 | 30 | 45 | 65 | 90 | 100 |  | 0 | 0 | 35 | 65 | 70 |
| NUTSEDGE |  |  | 20 | 40 | 70 | 85 | 100 | 100 |  | 0 | 0 | 40 | 75 | 100 |
| VELVETLEAF |  |  | 40 | 55 | 75 | 85 | 100 | 100 |  | 0 | 0 | 25 | 35 | 45 |
| COCKLEBUR |  |  | 20 | 30 | 40 | 55 | 70 | 90 |  | 0 | 30 | 40 | 60 | 90 |
| SMARTWEED |  |  | 30 | 55 | 75 | 90 | 100 | 100 |  | 35 | 75 | 100 | 100 | 100 |
| LAMBSQUARTER |  |  | 50 | 70 | 85 | 90 | 100 | 100 |  | 60 | 85 | 100 | 100 | 100 |
| PIGWEED |  |  | 30 | 55 | 75 | 90 | 95 | 100 |  | 30 | 60 | 95 | 100 | 100 |
| MORNINGGLORY |  |  | 30 | 45 | 65 | 85 | 95 | 100 |  | 25 | 50 | 85 | 100 | 100 |
| JIMSONWEED |  |  | 40 | 50 | 75 | 85 | 95 | 100 |  | 0 | 35 | 70 | 100 85 | 95 |
| POSTEMERGENCE | | | | | | | | | | | | | | |
| SOIL TYPE | A | A | A | A | A | A |  |  | A | A | A | A | A | A |
| CORN | 0 | 0 | 0 | 0 | 0 | 30 |  |  | 0 | 0 | 0 | 0 | 20 | 35 |
| SOYBEAN | 0 | 0 | 20 | 30 | 45 | 65 |  |  | 0 | 30 | 50 | 80 | 95 | 100 |
| GREEN FXTL | 0 | 0 | 0 | 0 | 0 | 0 |  |  | 0 | 0 | 0 | 25 | 50 | 65 |
| GIANT FXTL | 0 | 0 | 0 | 0 | 0 | 0 |  |  | 0 | 0 | 0 | 0 | 30 | 40 |
| PANICUM | 0 | 0 | 0 | 0 | 20 | 40 |  |  | 0 | 0 | 0 | 0 | 35 | 65 |
| CRABGRASS | 0 | 0 | 0 | 0 | 0 | 0 |  |  | 0 | 0 | 0 | 0 | 0 | 25 |
| BARNYARDGRASS | 0 | 0 | 0 | 0 | 0 | 35 |  |  | 0 | 0 | 0 | 0 | 35 | 70 |
| JOHNSONGRASS | 0 | 0 | 0 | 0 | 0 | 30 |  |  | 0 | 0 | 0 | 30 | 45 | 70 |
| SORGHUM | 0 | 0 | 25 | 50 | 60 | 65 |  |  | 0 | 20 | 35 | 65 | 75 | 80 |
| NUTSEDGE | 0 | 30 | 50 | 75 | 95 | 100 |  |  | 0 | 25 | 55 | 75 | 95 | 100 |
| VELVETLEAF | 25 | 50 | 65 | 85 | 100 | 100 |  |  | 0 | 0 | 35 | 45 | 70 | 90 |
| COCKLEBUR | 0 | 0 | 0 | 30 | 45 | 75 |  |  | 40 | 65 | 90 | 100 | 100 | 100 |
| SMARTWEED | 0 | 40 | 60 | 70 | 90 | 100 |  |  | 50 | 75 | 100 | 100 | 100 | 100 |
| LAMBSQUARTER | 0 | 0 | 30 | 50 | 65 | 85 |  |  | 35 | 50 | 75 | 80 | 90 | 95 |
| PIGWEED | 30 | 50 | 75 | 85 | 95 | 100 |  |  | 45 | 60 | 85 | 95 | 100 | 100 |
| MORNINGGLORY | 0 | 35 | 55 | 70 | 85 | 100 |  |  | 40 | 70 | 95 | 100 | 100 | 100 |
| JIMSONWEED | 20 | 40 | 60 | 75 | 95 | 100 |  |  | 60 | 75 | 90 | 100 | 100 | 100 |
| PERLIGHT CORN | 0 | 0 | 0 | 0 | 0 | 20 |  |  | 0 | 0 | 0 | 0 | 0 | 20 |

Test E

Sixteen cm diameter Wagner pots, equipped with a stoppered drain opening near the bottom of the side wall, were partially filled with Woodstown sandy loam. About 1500 mls of water were added to each pot to bring the water level to a point 3 cm above the soil surface. Japonica and Indica rice seedlings were hand transplanted into the pots. Also, an number of barnyardgrass (*Echinochloa crusgualli*) seeds were added to each

TABLE E

|  | CMPD 13 | |
|---|---|---|
| RATE = G/HA | 0016 | 0063 |
| SOIL | | |
| BARNYARD GRASS | 40 | 75 |
| WATER CHESTNUT | 65 | 72 |
| ARROWHEAD | 25 | 95 |
| SCIRPUS (SEDGE) | 90 | 80 |
| CYPRESS (SEDGE) | 60 | 90 |
| WATER PLANTAIN | 95 | 87 |

TABLE E-continued

| | | | |
|---|---|---|---|
| RICE JAP EFF | | 25 | 60 |

| | CMPD 13 | | |
|---|---|---|---|
| RATE = G/HA | 0004 | 0008 | 0016 |
| SOIL | | | |
| BARNYARD GRASS | 0 | 20 | 50 |
| WATER CHESTNUT | 0 | 20 | 0 |
| SCIRPUS (SEDGE) | 0 | 0 | 20 |
| CYPRESS (SEDGE) | 0 | 0 | 40 |
| WATER PLAINTAIN | 0 | 0 | 50 |
| RICE INDICA EFF | 0 | 0 | 0 |

| | CMPD 13 | | | |
|---|---|---|---|---|
| RATE = G/HA | 0004 | 0016 | 0063 | 0250 |
| SOIL | | | | |
| RICE JAP TOL | 0 | 35 | 45 | 50 |
| RICE INDICA TOL | 0 | 0 | 60 | 65 |

| | CMPD 14 |
|---|---|
| RATE = G/HA | 0063 |
| SOIL | |
| BARNYARD GRASS | 30 |
| WATER CHESTNUT | 25 |
| ARROWHEAD | 90 |
| SCIRPUS (SEDGE) | 60 |
| CYPRESS (SEDGE) | 60 |
| WATER PLAINTAIN | 95 |
| RICE JAP EFF | 5 |

| | CMPD 14 | | |
|---|---|---|---|
| RATE = G/HA | 0004 | 0016 | 0250 |
| SOIL | | | |
| RICE JAP TOL | 0 | 15 | 45 |

TABLE E-continued

| | | | |
|---|---|---|---|
| RICE INDICA TOL | 0 | 0 | 0 |

Test F

Two ten-inch diameter plastic pans lined with polyethylene liners were filled with prepared Fallsington silt loam soil. One pan was planted with seeds of wheat (*Triticum aestivum*), barley (*Hardeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), rapeseed (*Brassica napus*), an Italian ryegrass (*Lolium multiflorum*). The other pan was planted with seeds of Russian thistle (*Salsola kali*), speedwell (*Veronica persica*), kochia (*Kochia scoparia*), shepherd's purse (*Capsella bursa-pastoris*), Matricaria inodora, bedstraw (*Galium aparine*), black nightshade (*Solanum nigrum*), and wild buckwheat (*Polygonum convolvulus*). The above two pans were treated preemergence. At the same time two pans in which the above plant species were growing were treated postemergence. Plant height at the time of treatment ranged from 1–15 cm depending on plant species.

The compound was diluted in a non-phytotoxic solvent and sprayed over-the-top of the pan. An untreated control and a solvent alone were included for comparison. All treatments were maintained in the greenhouse for 20 days after which time the treatments were compared to the controls and the effects visually rated. The recorded data are presented in Table F.

TABLE F

| | CMPD 2 | | | | | | CMPD 9 | | | |
|---|---|---|---|---|---|---|---|---|---|---|
| RATE KG/HA | 0.004 | 0.008 | 0.016 | 0.032 | 0.064 | 0.125 | 0.032 | 0.064 | 0.125 | 0.25 |
| PREEMERGENCE | | | | | | | | | | |
| WHEAT | 0 | 0 | 0 | 0 | 0 | 0 | 0 | 0 | 0 | 0 |
| BARLEY | 0 | 0 | 0 | 0 | 20 | 20 | 0 | 0 | 0 | 0 |
| WILD OATS | 0 | 0 | 0 | 0 | 0 | 10 | 0 | 0 | 0 | 20 |
| CHEATGRASS | 0 | 0 | 0 | 0 | 10 | 30 | 0 | 0 | 10 | 30 |
| BLACKGRASS | 0 | 0 | 0 | 0 | 0 | 0 | 0 | 0 | 20 | 20 |
| ANN. BLUEGRASS | 0 | 0 | 0 | 0 | 0 | 20 | 0 | 0 | 0 | 0 |
| GREEN FOXTAIL | 0 | 0 | 0 | 20 | 50 | 80 | 20 | 50 | 60 | 75 |
| ITAL. RYEGRASS | 0 | 0 | 0 | 0 | 0 | 20 | 0 | 0 | 10 | 20 |
| RAPESEED | 40 | 80 | 90 | 90 | 90 | 100 | 0 | 20 | 70 | 90 |
| WINTER WHEAT | 0 | 0 | 0 | 0 | 0 | 10 | 0 | 0 | 0 | 0 |
| WINTER BARLEY | 0 | 0 | 0 | 20 | 30 | 40 | 0 | 0 | 0 | 0 |
| GOATGRASS | 0 | 0 | 0 | 0 | 0 | 10 | 0 | 0 | 0 | 0 |
| GALIUM | 20 | 50 | 50 | 70 | 80 | 90 | 0 | 0 | 20 | 70 |
| WILD BUCKWHEAT | 20 | 50 | 70 | 80 | 90 | 90 | 0 | 10 | 30 | 60 |
| KOCHIA | 0 | 10 | 30 | 40 | 60 | 70 | 0 | 0 | 0 | 20 |
| FALSE CAMOMILE | 0 | 20 | 80 | 80 | 100 | 100 | 50 | 60 | 70 | 90 |
| RUSSIAN THISTLE | 0 | 0 | 10 | 10 | 50 | 80 | 70 | 70 | 90 | 90 |
| SPEEDWELL | 0 | 0 | 20 | 20 | 70 | 90 | 0 | 0 | 20 | 20 |
| SUGARBEETS | 60 | 70 | 80 | 90 | 90 | 100 | 30 | 40 | 60 | 70 |
| VRNCA HDRAFOLIA | 30 | 50 | 70 | 70 | 90 | 90 | 40 | 50 | 60 | 80 |
| LAMBSQUARTER | 0 | 20 | 70 | 80 | 80 | 80 | 0 | 20 | 60 | 80 |
| FIELD PENNYCRES | 60 | 70 | 70 | 80 | 80 | 90 | 0 | 40 | 70 | 80 |
| VIOLA | 10 | 30 | 40 | 70 | 70 | 80 | 20 | 20 | 40 | 100 |
| | | | | | | | 0 | 0 | 50 | 70 |
| POSTEMERGENCE | | | | | | | | | | |
| WHEAT | 0 | 0 | 0 | 0 | 0 | 0 | 0 | 0 | 0 | 0 |
| BARLEY | 0 | 0 | 0 | 0 | 0 | 20 | 0 | 0 | 0 | 0 |
| WILD OATS | 0 | 0 | 0 | 0 | 0 | 0 | 0 | 0 | 0 | 20 |
| CHEATGRASS | 0 | 0 | 0 | 0 | 0 | 20 | 0 | 0 | 0 | 0 |
| BLACKGRASS | 0 | 0 | 0 | 0 | 0 | 0 | 0 | 0 | 0 | 0 |
| ANN. BLUEGRASS | 0 | 0 | 0 | 0 | 0 | 0 | 0 | 0 | 0 | 20 |
| GREEN FOXTAIL | 0 | 0 | 0 | 0 | 30 | 30 | 0 | 0 | 0 | 30 |
| ITAL. RYEGRASS | 0 | 0 | 0 | 0 | 10 | 20 | 0 | 0 | 0 | 0 |
| RAPESEED | 30 | 40 | 90 | 95 | 100 | 100 | 0 | 0 | 0 | 20 |
| WINTER WHEAT | 0 | 0 | 0 | 0 | 10 | 30 | 0 | 0 | 0 | 0 |
| WINTER BARLEY | 0 | 0 | 0 | 0 | 20 | 40 | 0 | 0 | 0 | 0 |
| GOATGRASS | 0 | 0 | 0 | 0 | 0 | 0 | 0 | 0 | 0 | 0 |
| WILD OATS STG 2 | 0 | 0 | 0 | 0 | 0 | 0 | 0 | 0 | 0 | 0 |
| BLACKGRASS STG2 | 0 | 0 | 0 | 0 | 0 | 0 | 0 | 0 | 0 | 0 |

TABLE F-continued

| RATE KG/HA | CMPD 2 | | | | | | CMPD 9 | | | |
|---|---|---|---|---|---|---|---|---|---|---|
| | 0.004 | 0.008 | 0.016 | 0.032 | 0.064 | 0.125 | 0.032 | 0.064 | 0.125 | 0.25 |
| GALIUM | 10 | 30 | 60 | 70 | 80 | 90 | 0 | 0 | 0 | 40 |
| WILD BUCKWHEAT | 50 | 60 | 60 | 80 | 90 | 90 | 0 | 0 | 0 | 0 |
| KOCHIA | 0 | 0 | 20 | 40 | 40 | 70 | 0 | 0 | 0 | 0 |
| FALSE CHAMOMILE | 50 | 70 | 90 | 90 | 90 | 100 | 0 | 0 | 10 | 30 |
| BLK. NIGHTSHADE | 20 | 30 | 40 | 70 | 70 | 70 | 0 | 0 | 20 | 50 |
| RUSSIAN THISTLE | 20 | 40 | 50 | 60 | 60 | 90 | 0 | 0 | 0 | 0 |
| SPEEDWELL | 0 | 0 | 10 | 40 | 50 | 70 | 0 | 0 | 0 | 50 |
| SUGARBEETS | 70 | 80 | 90 | 90 | 90 | 100 | 0 | 0 | 20 | 50 |
| VRNCA HDRAFOLIA | 20 | 20 | 40 | 60 | 70 | 70 | 0 | 0 | 20 | 60 |
| LAMBSQUARTER | 0 | 20 | 40 | 60 | 70 | 70 | 0 | 0 | 0 | 30 |
| FIELD PENNYCRES | 20 | 30 | 40 | 90 | 100 | 100 | 0 | 0 | 40 | 80 |
| VIOLA | 0 | 0 | 0 | 20 | 30 | 60 | 0 | 0 | 0 | 40 |

Test G

For the postemergence phase of the test, crop and weed species are planted in a Sassafras sandy loam soil (approximately 1% organic matter) one to three weeks before application so that they will be present as young plants at the time of treatment. Alternatively, for postemergence tests, plants are grown in a 50:50 mixture of commercially available potting mix and Sassafras soil. Plantings for the preemergence phase are made in a Tama silt loam soil (approximately 3% organic matter) the day before, or the day of treatment. Approximate planting depths are: corn and soybeans—3 to 4 cm; morningglory, cocklebur, and nutsedge—2.5 to 3 cm; velvetleaf, sicklepod, and sesbania—2 cm; all other species—0.5 cm.

The test chemicals are dissolved/suspended in a non-phytotoxic solvent in concentrations required to obtain the desired rate of application. The solutions or suspensions are then applied as soil/foliage sprays to the young plants (postemergence phase) and to the soil surfaces of the freshly planted containers (preemergence phase). Application is made utilizing an automatic spray machine at a spray volume of 374 liters per hectare. Immediately after treatment, the containers are transferred to a greenhouse and subsequently watered on a demand basis, taking care not to wet the foliage of the plants in the postemergence phase of the test.

The following species are included in the test:

| PLANT SPECIES | SCIENTIFIC NAME | APPROX. GROWTH STAGE AT POST APPLICATION |
|---|---|---|
| Grass Weeds: | | |
| barnyardgrass | Echinochloa crus-galli | 2-3 leaves |
| giant foxtail | Setaria faberi | 2-3 leaves |
| green foxtail | Setaris viridis | 2-3 leaves |
| johnsongrass | Sorghum halepense | 2-3 leaves |
| fall panicum | Panicum dichotomiflorum | 2-3 leaves |
| purple mutsedge | Cyperus rotundus | 2-3 leaves |
| signalgrass | Brachiaria platyphylla | 2-3 leaves |
| crabgrass | Digitaria sanguinalis | 2-3 leaves |
| Broadleaf Weeds: | | |
| velvetleaf | Abutilon theophrasti | 2-3 leaves |
| jimsonweed | Datura stramonium | 1-2 true leaves |
| hemp sesbania | Sesbania exaltata | 1st true leaf |
| sicklepod | Cassia obtusifolia | 1st true leaf |
| cocklebur | Xanthium pensylvanicum | 2nd true leaf |
| ivyleaf morningglory | Ipomoea hederacea | 1-2 true leaves |
| ladysthumb smartweed | Polygonum persicaria | 3-4 leaves |
| pigweed | Amaranthus retroflexus | 4-5 leaves |
| lambsquarters | Chenopodium album | 4-5 leaves |
| teaweed | Sida spinosa | 2-3 leaves |
| eastern black-nightshade | Solanum ptycanthum | 2nd true leaf |
| corn (Funk G4646) | Zea mays | 2-3 leaves |
| soybeans (Williams) | Glycine max | 1st trifoliate |

Visual plant response ratings are made approximately two and four weeks after treatment for the post- and pre-emergence phases, respectively. The ratings are made on a percentage scale of 0 to 100, where 0=no injury, and 100=death of plants. The ratings are summarized in Table G.

TABLE G

| RATE GM/H | CMPD 2 | | | | |
|---|---|---|---|---|---|
| | 0004 | 0008 | 0016 | 0031 | 0062 |
| POSTEMERGENCE | | | | | |
| SOIL TYPE | A | A | A | A | A |
| SOYBEAN | 20 | 30 | 70 | 70 | 85 |
| CORN | 0 | 0 | 0 | 20 | 30 |
| VELVTLEAF | 60 | 90 | 100 | 100 | 100 |
| JIMSONWEED | 70 | 70 | 80 | 85 | 100 |
| SICKLEPOD | 0 | 0 | 0 | 0 | 0 |
| SESBANIA | 85 | 90 | 100 | 100 | 100 |
| COCKLEBUR | 30 | 70 | 95 | 100 | 100 |
| IVYLEAF M/G | 30 | 40 | 60 | 70 | 80 |
| PURSLANE | | | | | |
| PIGWEED | 0 | 0 | 20 | 60 | 75 |
| LAMBSQUARTER | 20 | 70 | 85 | 85 | 90 |
| PRICKLY SIDA | 50 | 60 | 60 | 70 | 90 |
| BINDWEED | 50 | 85 | 95 | 100 | 100 |
| BARNYARDGRASS | 0 | 0 | 0 | 0 | 50 |
| GIANT FXTL | 0 | 0 | 0 | 0 | 0 |
| GREEN FXTL | 0 | 0 | 0 | 0 | 50 |
| JOHNSONGRASS | 0 | 0 | 0 | 0 | 50 |
| FALL PANICUM | 0 | 0 | 0 | 0 | 70 |
| CRABGRASS | 0 | 0 | 0 | 0 | 0 |
| SIGNALGRASS | 0 | 0 | 0 | 20 | 30 |
| NUTSEDGE | 50 | 85 | | 100 | 100 |
| SMARTWEED | 30 | 60 | 80 | 90 | 95 |
| RAGWEED | | | | | |
| NIGHTSHADE | | | | | |

| RATE GM/H | CMPD 2 | | | | |
|---|---|---|---|---|---|
| | 0016 | 0031 | 0062 | 0125 | 0250 |
| PREEMERGENCE | | | | | |
| SOIL TYPE | B | B | B | B | B |
| SOYBEAN | 0 | 20 | 30 | 40 | 70 |
| CORN | 0 | 0 | 0 | 35 | 60 |
| VELVTLEAF | 0 | 50 | 70 | 100 | 100 |
| JIMSONWEED | 70 | 90 | 90 | 100 | 100 |
| SICKLEPOD | 0 | 0 | 30 | 30 | 40 |
| SESBANIA | 20 | 50 | 85 | 90 | 100 |
| COCKLEBUR | 0 | 0 | 50 | 70 | 100 |

| | | CMPD 11 | | | |
|---|---|---|---|---|---|
| RATE GM/H | 0008 | 0016 | 0031 | 0062 | 0125 |
| | POSTEMERGENCE | | | | |
| SOIL TYPE | A | A | A | A | A |
| SOYBEAN | 0 | 0 | 25 | 55 | 70 |
| CORN | 0 | 0 | 0 | 20 | 30 |
| VELVTLEAF | 85 | 95 | 100 | 100 | 100 |
| JIMSONWEED | 0 | 0 | 50 | 85 | 95 |
| SICKLEPOD | 0 | 0 | 0 | 0 | 40 |
| SESBANIA | 50 | 75 | 85 | 95 | 100 |
| COCKLEBUR | 0 | 0 | 30 | 60 | 70 |
| IVYLEAF M/G | 0 | 0 | 75 | 75 | 75 |
| PIGWEED | 0 | 0 | 0 | 30 | 50 |
| LAMBSQUARTER | 0 | 0 | 0 | 0 | 30 |
| PRICKLY SIDA | 0 | 0 | 0 | 0 | 0 |
| BARNYARDGRASS | 0 | 0 | 0 | 20 | 30 |
| GIANT FXTL | 0 | 0 | 0 | 0 | 0 |
| GREEN FXTL | 0 | 0 | 0 | 0 | 0 |
| JOHNSONGRASS | 0 | 0 | 0 | 0 | 0 |
| FALL PANICUM | 0 | 0 | 0 | 0 | 0 |
| CRABGRASS | 0 | 0 | 0 | 0 | 0 |
| SIGNALGRASS | 0 | 0 | 0 | 0 | 0 |
| NUTSEDGE | 0 | 70 | 75 | 90 | 100 |
| SMARTWEED | 0 | 0 | 40 | 60 | 65 |
| NIGHTSHADE | 80 | 75 | 95 | 100 | 95 |

TABLE G-continued

| | | | | | |
|---|---|---|---|---|---|
| IVYLEAF M/G | 0 | 0 | 30 | 50 | 60 |
| PURSLANE | | | | | |
| PIGWEED | 80 | 80 | 95 | 100 | 95 |
| LAMBSQUARTER | 80 | 85 | 90 | 100 | 100 |
| PRICKLY SIDA | 30 | 80 | 85 | 90 | 95 |
| BINDWEED | 0 | 30 | | 60 | 100 |
| BARNYARDGRASS | 20 | 50 | 50 | 60 | 70 |
| GIANT FXTL | 0 | 20 | 30 | 50 | 60 |
| GREEN FXTL | 0 | 40 | 50 | 70 | 80 |
| JOHNSONGRASS | 0 | 50 | 60 | 70 | 90 |
| FALL PANICUM | 0 | 50 | 90 | 100 | 95 |
| CRABGRASS | 0 | 0 | 20 | 30 | 30 |
| SIGNALGRASS | 0 | 0 | 0 | 20 | 50 |
| NUTSEDGE | 40 | 60 | 80 | 90 | 100 |
| SMARTWEED | 30 | 70 | 85 | 95 | 95 |

| | | CMPD 14 | | | |
|---|---|---|---|---|---|
| RATE GM/H | 0008 | 0016 | 0031 | 0062 | 0125 |
| | POSTEMERGENCE | | | | |
| SOIL TYPE | A | A | A | A | A |
| SOYBEAN | 0 | 20 | 45 | 65 | 80 |
| CORN | 0 | 0 | 0 | 10 | 10 |
| VELVTLEAF | 70 | 90 | 100 | 100 | 100 |
| JIMSONWEED | 50 | 65 | 75 | 90 | 90 |
| SICKLEPOD | 0 | 0 | 0 | 0 | 20 |
| SESBANIA | 75 | 100 | 100 | 100 | 100 |
| COCKLEBUR | 30 | 50 | 60 | 70 | 85 |
| IVYLEAF M/G | 0 | 30 | 40 | 80 | 75 |
| PIGWEED | 0 | 0 | 0 | 0 | 40 |
| LAMBSQUARTER | 0 | 20 | 40 | 40 | 40 |
| PRICKLY SIDA | 0 | 0 | 0 | 20 | 40 |
| BARNYARDGRASS | 0 | 0 | 0 | 0 | 20 |
| GIANT FXTL | 0 | 0 | 0 | 0 | 0 |
| GREEN FXTL | 0 | 0 | 0 | 0 | 20 |
| JOHNSONGRASS | 0 | 0 | 0 | 0 | 0 |
| FALL PANICUM | 0 | 0 | 0 | 0 | 0 |
| CRABGRASS | 0 | 0 | 0 | 0 | 0 |
| SIGNALGRASS | 0 | 0 | 0 | 0 | 0 |
| NUTSEDGE | 60 | 70 | 75 | 85 | 95 |
| SMARTWEED | 0 | 30 | 50 | 80 | 100 |
| NIGHTSHADE | 30 | 60 | 60 | 75 | 90 |

I claim:

1. A compound having the formula:

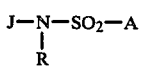

wherein

R is H, C(O)R$_1$, CO$_2$R$_1$', C(O)NR$_1$R$_2$, C(S)NR$_1$R$_2$, C$_3$-C$_4$ alkenyl or C$_3$-C$_4$ alkynyl;

R$_1$ is C$_1$-C$_4$ alkyl; C$_1$-C$_4$ haloalkyl; C$_2$-C$_4$ alkoxyalkyl; C$_3$-C$_4$ alkenyl; C$_3$-C$_4$ alkynyl or phenyl optionally substituted by F, Cl, Br, CH$_3$ or OCH$_3$;

R$_2$ is H or C$_1$-C$_2$ alkyl;

J is

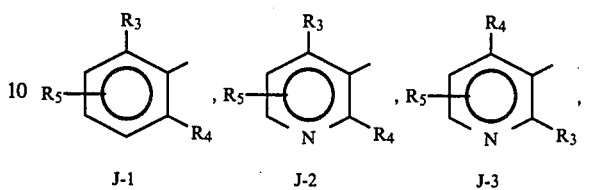

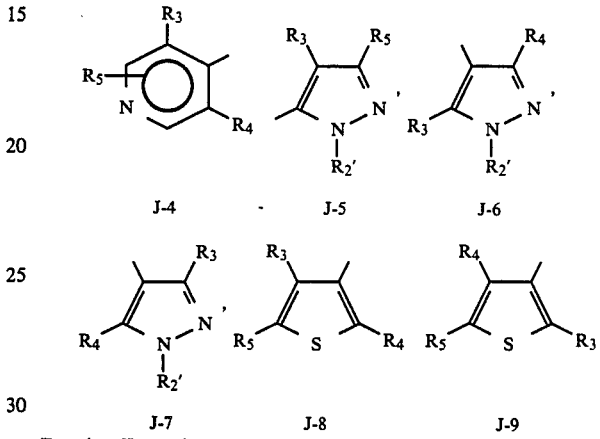

R$_3$ is F; Cl; Br; I; NO$_2$; ER$_1$''; C$_1$-C$_4$ alkyl; SO$_2$NR$_1$'''R$_2$; C$_1$-C$_4$ alkyl substituted by at least one F, Cl, Br or C$_1$-C$_3$ alkoxy; C(O)R$_1$''''; CO$_2$R$_1$'; OSO$_2$R$_1$'';

E is O, S, SO or SO$_2$;

R$_4$ is F; Cl; Br; I; NO$_2$; ER$_1$''; C$_1$-C$_4$ alkyl; C$_1$-C$_4$ alkyl substituted by at least one F, Cl, Br or C$_1$-C$_3$ alkoxy or OSO$_2$R$_1$'';

R$_5$ is H; F; Cl; Br; NO$_2$; N(CH$_3$)$_2$; E(C$_1$-C$_2$ alkyl); C$_1$-C$_2$ alkyl or C$_1$-C$_2$ alkyl substituted by at least one F, Cl, Br or OCH$_3$;

R$_1'$ is C$_1$-C$_4$ alkyl, C$_2$-C$_4$ haloalkyl, C$_2$-C$_4$ alkoxyalkyl, C$_3$-C$_4$ alkenyl or C$_3$-C$_4$ alkynyl;

R$_1''$ is C$_1$-C$_4$ alkyl, C$_1$-C$_4$ haloalkyl, C$_2$-C$_4$ alkoxyalkyl, C$_3$-C$_4$ alkenyl or C$_3$-C$_4$ alkynyl;

R$_1'''$ is C$_1$-C$_3$ alkyl, allyl or propargyl;

R$_1''''$ is C$_1$-C$_4$ alkyl, C$_1$-C$_4$ haloalkyl, C$_2$-C$_4$ alkoxyalkyl, C$_3$-C$_4$ alkenyl, C$_3$-C$_4$ alkynyl, cyclopropyl or cyclopropylmethyl;

R$_2'$ is H, C$_1$-C$_3$ alkyl, allyl, propargyl, CF$_3$CH$_2$, or phenyl;

R$_A$ is H or CH$_3$;

R$_B$ is H, CH$_3$ or CH$_2$CH$_3$;

A is

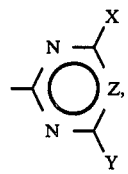   A-1

X is H, C$_1$-C$_4$ alkyl, C$_1$-C$_4$ alkoxy, C$_1$-C$_4$ haloalkoxy, C$_1$-C$_4$ haloalkyl, C$_1$-C$_4$ haloalkylthio, C$_1$-C$_4$ alkylthio, halogen, C$_2$-C$_5$ alkoxyalkyl, C$_2$-C$_5$ alkoxyalkoxy, amino, C$_1$-C$_3$ alkylamino, di(C$_1$-C$_3$ alkyl)amino or C$_3$-C$_5$ cycloalkyl;

Y is H, C$_1$-C$_4$ alkyl, C$_1$-C$_4$ alkoxy, C$_1$-C$_4$ haloalkoxy, C$_1$-C$_4$ haloalkylthio, C$_1$-C$_4$ alkylthio, C$_2$-C$_5$ alkoxyalkyl, C$_2$-C$_5$ alkoxyalkoxy, amino, C$_1$-C$_3$ alkylamino, di(C$_1$-C$_3$ alkyl)amino, C$_3$-C$_4$ alkenyloxy, C$_3$-C$_4$ alkynyloxy, C$_2$-C$_5$ alkylthioalkyl, C$_2$-C$_5$ alkylsulfinylalkyl, C$_2$-C$_5$ alkylsulfonylalkyl, C$_1$-C$_4$ haloalkyl, azido,

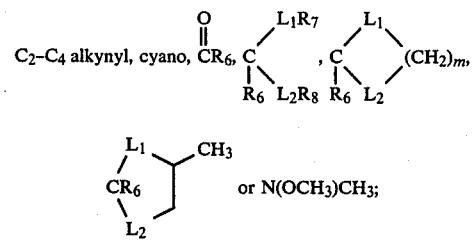

or N(OCH$_3$)CH$_3$;

m is 2 or 3;

L$_1$ and L$_2$ are independently O or S;

R$_6$ is H or C$_1$-C$_3$ alkyl;

R$_7$ and R$_8$ are independently C$_1$-C$_3$ alkyl;

Z is CH, CCH$_3$, CC$_2$H$_5$, CCl or CBr;

provided that (a) when X is Cl, F, Br or I, then Y is OCH$_3$, CO$_2$H$_5$, N(OCH$_3$)CH$_3$, NHCH$_3$, N(CH$_3$)$_2$ or OCF$_2$H; and (b) when the total number of carbon atoms of X and Y is greater than four, then the combined number of carbons of R$_3$, R$_4$ and R$_5$ is less than or equal to six.

2. A compound of claim 1 wherein

R is H;

X is CH$_3$, OCH$_3$, OCH$_2$CH$_3$, Cl, F, Br, I, OCF$_2$H, CH$_2$F, CF$_3$, OCH$_2$CH$_2$F, OCH$_2$CHF$_2$, OCH$_2$CF$_3$, CH$_2$Cl or CH$_2$Br;

Y is H, CH$_3$, OCH$_3$, OCH$_2$CH$_3$, CH$_2$OCH$_3$, NHCH$_3$, N(OCH$_3$)CH$_3$, N(CH$_3$)$_2$, CH$_2$CH$_3$, CF$_3$, SCH$_3$, OCH$_2$CH=CH$_2$, OCH$_2$C≡CH, CH$_2$OCH$_2$CH$_3$, OCH$_2$CH$_2$OCH$_3$, CH$_2$SCH$_3$, CH$_2$SCH$_2$CH$_3$, OCH$_2$CH$_2$OCH$_3$,

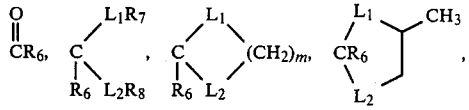

OCF$_2$H, SCF$_2$H, C≡CH and C≡CCH$_3$.

3. A compound of claim 2 wherein J is J-1.
4. A compound of claim 2 wherein J is J-2.
5. A compound of claim 2 wherein J is J-3.
6. A compound of claim 2 wherein J is J-4.
7. A compound of claim 2 wherein J is J-5.
8. A compound of claim 2 wherein J is J-6.
9. A compound of claim 2 wherein J is J-7.
10. A compound of claim 2 wherein J is J-8.
11. A compound of claim 2 wherein J is J-9.
12. A compound of claim 3 wherein
R$_5$ is H, F, Cl, Br, CH$_3$, OCH$_3$ or SCH$_3$.
13. A compound of claim 12 wherein
X is CH$_3$, OCH$_3$, OCH$_2$CH$_3$, Cl or C$_1$-C$_2$ haloalkoxy and
Y is CH$_3$, OCH$_3$, CH$_2$CH$_3$, CH$_2$OCH$_3$, C$_1$-C$_2$ haloalkoxy, NHCH$_3$ or N(CH$_3$)$_2$.
14. A compound of claim 13 wherein
R$_5$ is H;
R$_3$ is F, Cl, Br, E(C$_1$-C$_2$ alkyl), C$_1$-C$_2$ alkyl, SO$_2$NHCH$_3$, SO$_2$N(CH$_3$)$_2$, C$_1$-C$_2$ alkyl substituted by at least one F, Cl, Br or OCH$_3$, C(O)(C$_1$-C$_2$ alkyl), CO$_2$(C$_1$-C$_2$ alkyl) or OSO$_2$(C$_1$-C$_2$ alkyl); and
R$_4$ is F, Cl, Br, E(C$_1$-C$_2$ alkyl), C$_1$-C$_2$ alkyl, SO$_2$NHCH$_3$, SO$_2$N(CH$_3$)$_2$, C$_1$-C$_2$ alkyl substituted by at least one F, Cl, Br or OCH$_3$, C(O)(C$_1$-C$_2$ alkyl), CO$_2$(C$_1$-C$_2$ alkyl) or OSO$_2$(C$_1$-C$_2$ alkyl).

15. The compound of claim 1 which is N-(2-chloro-6-methylphenyl)-4,6-dimethyl-2-pyrimidinesulfonamide.

16. The compound of claim 1 which is N-(2,6-dichlorophenyl)-4,6-dimethyl-2-pyrimidinesulfonamide.

17. The compound of claim 1 which is N-(2,6-dichloro-3-methylphenyl)-4,6-dimethyl-2-pyrimidinesulfonamide.

18. The compound of claim 1 which is N-(2,6-dichlorophenyl)-4,6-dimethoxy-2-pyrimidinesulfonamide.

19. The compound of claim 1 which is N-(2,6-dichlorophenyl)-4-methoxy-6-methyl-2-pyrimidinesulfonamide.

20. A composition suitable for controlling the growth of undesired vegetation which comprises an effective amount of a compound of claim 1 and at least one of the following: surfactant, solid or liquid diluent.

21. A composition suitable for controlling the growth of undesired vegetation which comprises an effective amount of a compound of claim 2 and at least one of the following: surfactant, solid or liquid diluent.

22. A composition suitable for controlling the growth of undesired vegetation which comprises an effective amount of a compound of claim 3 and at least one of the following: surfactant, solid or liquid diluent.

23. A composition suitable for controlling the growth of undesired vegetation which comprises an effective amount of a compound of claim 4 and at least one of the following: surfactant, solid or liquid diluent.

24. A composition suitable for controlling the growth of undesired vegetation which comprises an effective amount of a compound of claim 5 and at least one of the following: surfactant, solid or liquid diluent.

25. A composition suitable for controlling the growth of undesired vegetation which comprises an effective amount of a compound of claim 6 and at least one of the following: surfactant, solid or liquid diluent.

26. A composition suitable for controlling the growth of undesired vegetation which comprises an effective amount of a compound of claim 7 and at least one of the following: surfactant, solid or liquid diluent.

27. A composition suitable for controlling the growth of undesired vegetation which comprises an effective amount of a compound of claim 8 and at least one of the following: surfactant, solid or liquid diluent.

28. A composition suitable for controlling the growth of undesired vegetation which comprises an effective amount of a compound of claim 9 and at least one of the following: surfactant, solid or liquid diluent.

29. A composition suitable for controlling the growth of undesired vegetation which comprises an effective amount of a compound of claim 10 and at least one of the following: surfactant, solid or liquid diluent.

30. A composition suitable for controlling the growth of undesired vegetation which comprises an effective amount of a compound of claim 11 and at least one of the following: Surfactant, solid or liquid diluent.

31. A method for controlling the growth of undesired vegetation which comprises applying to the locus to be protected an effective amount of a compound of claim 1.

32. A method for controlling the growth of undesired vegetation which comprises applying to the locus to be protected an effective amount of a compound of claim 2.

33. A method for controlling the growth of undesired vegetation which comprises applying to the locus to be protected an effective amount of a compound of claim 3.

34. A method for controlling the growth of undesired vegetation which comprises applying to the locus to be protected an effective amount of a compound of claim 4.

35. A method for controlling the growth of undesired vegetation which comprises applying to the locus to be protected an effective amount of a compound of claim 5.

36. A method for controlling the growth of undesired vegetation which comprises applying to the locus to be protected an effective amount of a compound of claim 6.

37. A method for controlling the growth of undesired vegetation which comprises applying to the locus to be protected an effective amount of a compound of claim 7.

38. A method for controlling the growth of undesired vegetation which comprises applying to the locus to be protected an effective amount of a compound of claim 8.

39. A method for controlling the growth of undesired vegetation which comprises applying to the locus to be protected an effective amount of a compound of claim 9.

40. A method for controlling the growth of undesired vegetation which comprises applying to the locus to be protected an effective amount of a compound of claim 10.

41. A method of controlling the growth of undesired vegetation which comprises applying to the locus to be protected an effective amount of a compound of claim 11.

* * * * *